United States Patent [19]

Billiar et al.

[11] Patent Number: 5,830,461
[45] Date of Patent: Nov. 3, 1998

[54] METHODS FOR PROMOTING WOUND HEALING AND TREATING TRANSPLANT-ASSOCIATED VASCULOPATHY

[75] Inventors: Timothy R. Billiar; Edith Tzeng, both of Pittsburgh; Larry L. Shears, II, Bethel Park; David A. Geller; Howard David James Edington, both of Pittsburgh, all of Pa.

[73] Assignee: University of Pittsburgh of the Commonwealth System of Higher Education, Pittsburgh, Pa.

[21] Appl. No.: 745,375

[22] Filed: Nov. 8, 1996

Related U.S. Application Data

[63] Continuation-in-part of Ser. No. 630,798, Apr. 10, 1996, which is a continuation-in-part of Ser. No. 265,046, Jun. 24, 1994, Pat. No. 5,658,565, and Ser. No. 465,522, Jun. 5, 1995, which is a division of Ser. No. 314,917, Sep. 28, 1994, Pat. No. 5,468,630, which is a continuation of Ser. No. 981,344, Nov. 25, 1992, abandoned.

[51] Int. Cl.$^6$ ............................. A61K 38/44; C12N 9/02
[52] U.S. Cl. ..................... 424/94.4; 435/189; 424/94.1
[58] Field of Search .................. 424/94.1, 94.4; 435/189

[56] References Cited

U.S. PATENT DOCUMENTS

| | | | |
|---|---|---|---|
| 4,840,940 | 6/1989 | Sottiuri | 514/56 |
| 5,132,407 | 7/1992 | Stuehr et al. | 530/395 |
| 5,252,479 | 10/1993 | Srivastava | 435/320.1 |
| 5,304,121 | 4/1994 | Shahatjian | 604/53 |
| 5,328,470 | 7/1994 | Nabel et al. | 604/101 |
| 5,428,070 | 6/1995 | Cooke et al. | 514/537 |

FOREIGN PATENT DOCUMENTS

| | | |
|---|---|---|
| WO 92/07573 | 5/1992 | WIPO . |
| WO 94/23038 | 10/1994 | WIPO . |
| WO 94/24269 | 10/1994 | WIPO . |
| WO9600006 | 1/1996 | WIPO . |
| WO9605319 | 2/1996 | WIPO . |
| WO9733980 | 9/1997 | WIPO . |

OTHER PUBLICATIONS

Shabani et al., *Wound Repair and Regeneration*, 4(3,) 353–362 (1996).
Shears et al., *Proceedings for the 51$^{st}$ Annual Sessions of the Owen H. Wangensteen Surgical Forum*, 451–45 (1996).
Von Der Leyen et al., *Proceeding of the National Academy of Science USA*, 92, 1137–1141 (1995).
Tzeng et al., *Proceeding of the National Academy of Science USA*, 92, 11771–11775 (1995).
Shears et al., *Journal of Clinical Investigation*, 100(8) 2035–2042 (1997).
Albina et al., *J. Immunol.*, 150(11), 5080–5085 (1993).
Billiar, et al., *Biochem. Biophys. Res. Comm.*, 168, 1034–1040 (1990).
Billiar, et al., *J. Leuk. Biol.*, 48, 565–569 (1990).
Bredt, et al., *Nature*, 351, 714–718 (1991).
Bucala, et al., *J. Clin. Invest.* 87, 432–438 (1991).
Busse and Mülsch, *FEBS Letters*, 265, 133–136 (1990).
Charles et al., *Proc. Natl. Acad. Sci. USA*, 90, 11419–11423 (1993).
Chester, et al., *Lancet*, 336, 897–900 (1990).
Chénais et al., *Biochem. Biophys. Res. Commun.*, 196, 1558–63 (1993).
Chin, et al., *J. Clin Invest.*, 89, 10–18 (1992).
Curran, et al., *J. Exp. Med.*, 170, 1769–1774 (1989).
Danos and Mulligan, *Proc. Natl. Acad. Sci. USA*, 85, 6460–6464 (1988).
Draiper, et al., *Res. Immunol.*, 142, 553–602 (1991).
Gao and Huang, *Biochm. Biophys. Res. Comm.*, 179, 280–285 (1991).
Geller, et al., *Proc. Natl. Acad. Sci. USA*, 90, 3491–3495 (1993).
Granger, et al., *J. Clin. Invest.*, 81, 1129–1136 (1988).
Green, et al., *J. Leuk. Biol.*, 50, 93–103 (1991).
Gross, et al., *Biochem. Biophys. Res. Comm.*, 178, 823–829 (1991).
Harbrecht, et al., *J. Leuk. Biol.*, 52, 390–394(??).
Hibbs, et al., *J. Immun.*, 138, 550–565 (1987).
Hibbs, et al., *Science*, 235, 473–476 (1987).
Ignarro, et al. *Proc. Natl. Acad. Sci. USA*, 84, 9265–9269 (1987).
Janssens, et al., *J. Biol. Chem.*, 267, 14519–14522 (1992).
Kilbourn, et al., *Proc. Natl. Acad. Sci. USA*, 87, 3629–3632 (1990).
Lowenstein, et al., *Proc. Natl. Acad. Sci. USA*, 89, 6711–6715 (1992).
Lyons, et al., *J. Biol. Chem.*, 267, 6370–6374 (1992).
Mannino and Gould-Fogerite, *BioTechniques*, 6, 682–690 (1988).
Mardsen, et al., *FEBS Letters*, 307, 287–293 (1992).
McNamara, et al., *Biochm. Biophys. Res. Comm.*, 193(1), 291–296 (1993).
Miller, *Current Topics in Microbiology and Immunology*, 158, 1–24 (1992).
Moncada, et al., *Pharmacological Reviews*, 43, 109–142 (1991).
Muzyczka, *Current Topics in Microbiology and Immunology*, 158, 97–129 (1992).
Nabel, et al., *Science*, 244, 1342–1344 (1989).
Nabel, et al., *Science*, 249, 1285–1288 (1990).
Nakayama, et al., *Am. J. Respir. Cell Mol. Biol.*, 7, 471–476 (1992).
Nunokawa and Tanaka, *Biochem. Biophys. Res. Comm.*, 188, 409–415, (1992).
Nussler, et al. *FASEB J.*, 6, 5:A1834#5200 (1992).
Nussler, et al., *J. Exp. Med.*, 176, 261 (1992).
Palmer, et al., *Nature*, 327, 524–525 (1987).

*Primary Examiner*—Dian C. Jacobson
*Attorney, Agent, or Firm*—Leydig, Voit & Mayer, Ltd.

[57] ABSTRACT

The present invention provides a method of promoting the closure of a wound in a patient. This method involves transferring exogenous iNOS to the region of the wound whereby a product of iNOS is produced in the region of the wound to promote the closure of the wound.

8 Claims, 8 Drawing Sheets

OTHER PUBLICATIONS

Radomski, et al., *Br. J. Pharmac.*, 92, 639–646 (1987).
Rosenberg, *Human Gene Therapy*, 3, 57–73 (1992).
Stribling et al., *Proc. Natl. Acad. Sci. USA*, 89, 11277–11281 (1992).
Stuehr et al., *J. Biol. Chem.*, 266, 6259–6263 (1991).
von der Leven, et al., *FASEB J.*, 8, A802 #4651 (1994).
Werner–Felmayer, et al., *J. Exp. Med.*, 172, 1599–1607 (1990).
Wilson, et al. *Science*, 244, 1344–1346 (1989).
Xie, et al., *Science*, 256, 225–228 (1992).
Zwiebel, et al., *Science*, 243, 220–22 (1989).

DFG-iNOS-Neo:

METHODS FOR PROMOTING WOUND HEALING AND TREATING TRANSPLANT-ASSOCIATED VASCULOPATHY

CROSS-REFERENCE TO RELATED APPLICATIONS

This application is a continuation-in-part of U.S. patent application Ser. No. 08/630,798, filed Apr. 10, 1996, and which is a continuation-in-part of U.S. patent application Ser. No. 08/265,046, filed Jun. 24, 1994, now U.S. Pat. No. 5,658,565, and a continuation-in-part of U.S. patent application Ser. No. 08/465,522, filed Jun. 5, 1995, which is a divisional of U.S. patent application Ser. No. 08/314,917, filed Sep. 28, 1994, now U.S. Pat. No. 5,468,630, which is a continuation of U.S. patent application Ser. No. 07/981,344, filed Nov. 25, 1992, now abandoned.

STATEMENT AS TO RIGHTS TO INVENTIONS MADE UNDER FEDERALLY SPONSORED RESEARCH AND DEVELOPMENT

This invention was made with Government support under Grant Number GM44100 awarded by the United States National Institutes of Health. The United States Government may have certain rights in this invention.

TECHNICAL FIELD OF THE INVENTION

The present invention relates to methods for promoting wound closure (i.e., healing) and treating of transplant-associated vasculopathy.

BACKGROUND OF THE INVENTION

1. NO Physiology

Nitric oxide (NO) is a biologically active compound derived from L-arginine. NO has disparate physiological roles, from intercellular signaling to toxicity, depending upon its concentration and location within an animal (reviewed in Moncada et al., *Pharm. Rev.*, 43(2) 109–42 (1991); Morris & Billiar, *Am. Phsiol. Soc.*, E829–37 (1994); Schmidt & Walter, *Cell*, 78, 919–25 (1994); Fedlman et al., *C. & E. N.*, 71, 26–38 (1993)).

Nitric oxide is normally produced by the vascular endothelium, but because of a very short half-life (t½ in seconds), it diffuses only to the adjacent smooth muscle where it causes relaxation of vascular smooth muscles via the activation of soluble guanylate cyclase (Moncada et al., *Pharmacol. Rev.*, 43, 109–42 (1991)). Nitric oxide released toward the lumen assists in preventing platelet adherence. The small amounts of nitric oxide derived from endothelial cells is produced in an ongoing fashion (Palmer et al., *Nature*, 327, 524–26 (1987); Ignarro et al., *Proc. Natl. Acad. Sci. USA*, 84, 9265–69 (1987)) by an enzyme (eNOS), which is located primarily on microsomal and plasma membranes.

Nitric oxide is known to be important to vascular integrity and the prevention of atherosclerotic lesions by promoting vasodilation (Palmer et al., supra; Ignarro et al., spra), inhibiting platelet adherence and aggregation (Radomski et al., *Br. J. Pharmacol.*, 92, 639–46 (1987)), inhibiting vascular smooth muscle (Nunokawa et al., *Biochem. Biophys. Res. Com.*, 188, 409–15 (1992)) and fibroblast (Werner-Felmayer et al., *J. Exp. Med.*, 172, 1599–1607 (1990)) cellular proliferation.

Several conditions can result in decreased NO production within an individual. For example, in certain forms of diabetes, patients experience decreased production of NO. Furthermore, certain modes of steroid therapy inhibit production of NO. While decreased NO production is itself a cause for concern, such NO-deficiency contributes to unwelcome complications, for example, in healing wounds.

In some instances excessive production of nitric oxide is detrimental. For example, inducement of nitric oxide synthesis in blood vessels by bacterial endotoxins, such as, for example, bacterial lipopolysaccharide (LPS), and cytokines that are elevated in sepsis results in excessive dilation of blood vessels and sustained hypotension commonly encountered with septic shock (Kilbourn et al., *Proc. Natl. Acad. Sci. USA*, 87, 3629–32 (1990)). Overproduction of nitric oxide in lungs stimulated by immune complexes directly damages the lung (Mulligan et al., *J. Immunol.*, 148, 3086–92 (1992)). Overproduction of nitric oxide in pancreatic islets impairs insulin secretion and contributes to the onset of juvenile diabetes (Corbett et al., *J. Biol. Chem.*, 266, 21351–54 (1991)). Production of nitric oxide in joints in immune-mediated arthritis contributes to joint destruction (McCartney et al., *J. Exp. Med.*, 178, 749–54 (1993)).

2. Nitric Oxide Synthase

NO is synthesized from L-arginine through a reaction catalyzed by an enzyme referred to as nitric oxide synthase (NOS), of which there are three known isoforms. Two isoforms are constitutive NOS exhibiting strict dependence upon intracellular calcium and produce NO constitutively but in small quantities. One of these isoforms (nNOS or NOS-1) is localized primarily in the CNS, and the other (eNOS or NOS-3) is a membrane-bound protein found primarily in endothelial cells (Morris & Billiar, supra). The third NOS is inducible nitric oxide synthase (iNOS), which exhibits tonic catalytic activity for the life of the enzyme, and functions without requiring an increace in intracellular calcium concentration.

NOS-mediated catalytic production of NO from arginine requires the presence of a cofactor, tetrahydrobiopterin ($BH_4$) (Tzeng et al., *Proc. Nat. Acad. Sci. USA*, 92, 11771–75 (1995); Tzeng et al., *Surgery*, 120(2), 315–21 (1995)). $BH_4$ is necessary, in part, for maintaining the active structural configuration of the enzyme. Most cells express GTP cyclohydrolase I (GTPCH), which is the rate-limiting enzyme required for de novo $BH_4$ synthesis. However, some tissues, such as vascular smooth muscle, express GTPCH only upon induction by cytokines (Tzeng et al., *Surgery*, 120(2), 315–21 (1995)).

iNOS expression increases dramatically in wound tissue (Carter et al., *Biochem J.*, 304, 201–04 (1994); see also Shabani et al., *Wound Healing Repair and Regeneration*, 4(3), 353–62 (1996)). Furthermore, iNOS is expressed in various tissues in response to inflammatory stimulation by cytokines, and iNOS has been cloned and isolated from hepatocytes so stimulated. U.S. Pat. No. 5,468,630, issued to Billiar et al. on Nov. 21, 1995, discloses the human hepatocyte iNOS cDNA sequence. The plasmid pHINOS comprises the human iNOS coding region and was deposited under the terms of the Budapest Treaty on Nov. 20, 1992 and has the ATCC accession number 75358 (pHINOS) and ATCC accession number 69126 (pHINOS transformed in *E. coli* SOLR).

Sustained production of nitric oxide by iNOS has antimicrobial and antitumor functions. (see Granger et al., *J. Clin. Invest.*, 81, 1129–36 (1989), and Hibbs et al., *Science*, 235, 473–76 (1987), respectively). Furthermore, when vascular smooth muscle cells are stimulated to express a iNOS enzyme by inflammatory cytokines, the large amounts of nitric oxide released contribute to the vasodilation and hypotension seen in sepsis (Busse and Mulsch, *FEBS Letters*, 265, 133–36 (1990)).

While termed "Nitric Oxide Synthase," iNOS-mediated catalysis produces other biologically active products. For example, N-hydroxyarginine, an intermediate byproduct of the iNOS enzyme (Stuehr et al., *J. Biol. Chem.,* 266, 6259–63 (1991)), is known to induce cytostasis in proliferating cells in a dose dependent manner (Chénais et al., *Biochem. Biophys. Res. Commun.,* 196, 1558–63 (1993)). Furthermore, NO itself acts in a dose-dependent manner, low concentrations being sufficient to mediate vasodilation while greater concentrations are required for cytostasis.

In light of its constitutive activity, the complex admixture of its biologically active products, and the capacity of its products to promote cytostasis among proliferating cells, delivery of exogenous iNOS appears an attractive method for treating disorders associated with hyperplasia. In fact, iNOS expression cassette transfer in vitro and in vivo has been demonstrated to achieve prophylactic and therapeutic relief from disorders associated with vascular occlusions (Tzeng et al., *Mol. Med.,* 2(2), 211–25 (1996); see also International Patent Application No. WO 96/00006, (Billiar et al.)).

3. Transplant Vasculopathy

Following transplantation of graft tissue, a patient is at risk for rejection of the graft. Generally, graft rejection is characterized as either acute or chronic, based upon the mechanisms for rejection. As advances have been made in surgical technique, organ handling, management of acute graft rejection episodes, and control of post-operative infection, the threat of acute rejection of grafts has steadily declined (Paul & Tilney, "Alloantigen-Dependent Events in Chronic Rejection," in *Transplantation Biology, Cellular and Molecular Aspects,* Tilney et al., eds., Raven Pubs., Philadelphia, 567 (1996)). However, the threat of chronic graft rejection has not changed significantly, and it remains a significant risk to graft transplant procedures. For example, most kidney transplant failure not attributed to patient death is due to chronic rejection; roughly 60% of all heart transplant recipients and 50% of lung transplant recipients, respectively, develop manifestations of chronic rejection (Id.; see also Libbey, "Transplantation-Associated Arteriosclerosis, Potential Mechanisms," in *Transplantation Biology, Cellular and Molecular Aspects,* Tilney et al., eds., Raven Publishers, Philadelphia, 577 (1996); Hosenpud, *Transplant Immunol.,* 1, 237–49 (1993)).

While the mechanisms causing the manifestation of chronic rejection remain poorly understood (Hosenpud, supra, page 237), the pathologic characteristics have been well defined. Vascular smooth muscle cells transform from a quiescent contractile phenotype to a rapidly proliferating phenotype. The proliferating smooth muscle cells invade the vascular lumen where they produce extracellular matrix material. Chronic rejection is thus characterized by progressive neointimal hyperplasia in vascular tissues, resulting in intimal thickening and eventual occlusion of vascular lumens in graft tissue (Hosenpud, supra; Ventura et al., *Curriculum in Cardiology,* 129 (4), 791–99 (1995); Libbey, supra). This presentation appears similar for transplanted heart, lung, and kidney tissue (Paul and Tilney, supra).

In comparison with naturally occurring arteriosclerosis (which is also produced by proliferating vascular smooth muscle cells, and is characterized by focal, and often eccentric, stenoses in large vessels) chronic rejection usually involves concentric arteriosclerosis extending over large regions of both large and small penetrating vessels. Moreover, chronic rejection arteriosclerosis develops extremely rapidly (Ventura et al., supra).

Efforts at preventing and treating allograft vasculopathy have met with only limited success. Advances in immunosuppression have failed to reduce the onset of chronic rejection (Ventura et al., supra, page 796). Some limited success has been reported with calcium-blocking agents and surgical intervention (Id., pages 796–97), but there is little evidence that these procedures influence long-term outcome (Hosenpud, supra). To date, re-transplantation is the primary mode of treatment for transplant-associated vasculopathy in heart grafts. However, due to the shortage of organs and the decreased short-term survival of patients receiving a second graft, this mode of treatment is not desirable.

Currently, there exists a need for an effective method of treating or preventing chronic graft rejection requiring minimal invasiveness and depletion of the supply of available organs.

4. Wound Healing

Closure of an open wound generally proceeds systematically through the processes of inflammation, repair and closure, remodeling, and final healing (reviewed in Hammar, *Int. J. Dermatol.,* 32(1), 6–15 (1993)). Throughout this sequence, a continuing interaction between diverse cell types is mediated through various intercellular molecules. Notably, cytokines, such as Platelet Derived Growth Factor, Transforming Growth Factor-β, and Fibroblast Growth Factor, etc., are important to normal wound closure (i.e., healing) (Id.). Furthermore, arginine metabolism and NO synthesis are increased as a result of wounding (see Shabani et al., *Wound Healing Repair and Regeneration,* 4(3), 353–62 (1996)).

Many wounds do not complete the healing process. In many patients, such as elderly patients (Kirk et al, *Surgery,* 114(2), 155–60 (1993), or those suffering from other complications, wounds may persist chronically or wounds may heal incompletely (Hammer, supra, page 6). These patients are more prone to secondary infections or other complications. Several of these other complications, such as in patients undergoing steroid treatment or diabetic patients, are also associated with reduced NO production.

Indeed, supply of exogenous arginine, the catalytic substrate for NOS enzymes, has been demonstrated to accelerate the healing of wounds in animal experiments (Seifer et al., *Surgery,* 84, 224–30 (1978); Barbul et al., *Am. J. Clin. Nutr.,* 37, 786–94 (1983)). Arginine stimulates wound healing in elderly human patients (Kirk et al., supra), and may act in part through stimulation of NO synthesis (Barbul et al., *Surgery,* 108(2), 331–37 (1990) (see appended dialog section)). Furthermore, direct topical administration of exogenous NO promotes healing of both chronic and normal wounds (Shabani et al., supra).

Several possible vehicles have been contemplated to deliver NO to wounds to promote healing (discussed in Shabani, supra). Some of these are delivered as pro-drugs, and thus require enzyme activation by means of electron transfer. Furthermore, the solubility of these pro-drugs renders them unlikely candidates for discrete targeting without systemic effects. Other methods involve a synthetic vehicle (a "NONOate") for delivery of NO to the site in question. Many of these are water-soluble and thus are difficult to contain within a wound site. Those which are not water soluble may become progressively less efficient in transferring NO to the wound as the healing process produces new tissue between the NONOate and the wound (Shabani, supra, page 360). Furthermore, use of topical NO delivery to internal wounds would require subsequent surgical invasions to remove the synthetic NO source. Additionally, therapies such as these only deliver one compound to a wound, where natural synthetic pathways leading to NO production also produce other biologically active compounds. Lastly, a constitutive source of exogenous NO may be counter-therapeutic in some applications, as NO is known to cause substantial tissue damage in excessive concentrations.

Thus, there exists a need for a method of promoting the closure or healing of chronic wounds. Additionally, there exists a need for facilitating the closure and healing of internal and external wounds in patients with reduced NO production. Furthermore, there exists a need for facilitating the closure and healing of internal and external wounds in patients with minimal invasiveness and without requiring application of foreign synthetic polymers. Lastly, there exists a need to employ a source of NO and other therapeutically-active compounds to a wound in a manner that prevents oversupply of NO.

BRIEF SUMMARY OF THE INVENTION

The present invention provides a method of promoting the closure (i.e., healing) of a wound in a patient. This method involves transferring exogenous iNOS to the region of the wound whereby a product of iNOS is produced in the region of the wound to promote the closure (i.e., healing) of the wound. The present inventive method applies to internal and external wounds, and preferably confines the production of biologically active products to the site in question, while being minimally invasive.

The invention may best be understood with reference to the accompanying drawings and in the following detailed description of the preferred embodiments.

DESCRIPTION OF THE PREFERRED EMBODIMENTS

1. DEFINITIONS

Figure 1A:
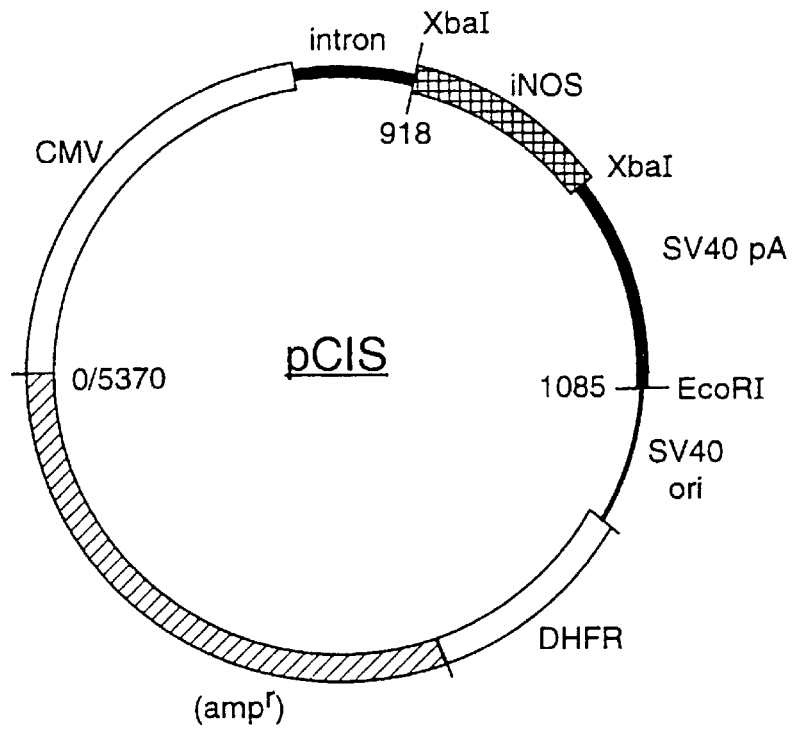
FIGS. 1A–B are schematic representations of the pCIS-iNOS vector (FIG. 1A) and the pCIS-GTPCH vector (FIG. 1B) utilized to exemplify suitable non-viral vectors to transfer expression cassettes. CMV indicates the cytomegalovirus enhancer/promoter polynucleotide; intron indicates a sequence from CMV; iNOS indicates a cDNA encoding human iNOS; GTPCH indicates a cDNA encoding GTP cyclohydrolase I, SV40pA indicates the polyadenylation sequence from SV40, SV40ori indicates the origin of replication polynucleotide from SV40; DHFR indicates a polynucleotide encoding dihydrofolate reductase, and amp$^r$ indicates a polynucleotide encoding β-lactamase.

As used herein, including the claims appended hereto, the following terms mean:

$BH_4$ denotes tetrahydrobiopterin, an essential cofactor for iNOS enzymatic activity.

A nucleic acid is expressed if it is transcribed into an RNA transcript.

An expression cassette comprises a polynucleotide for expression operably linked to a promoter. As used herein, when an expression cassette is identified by a particular translation product, the polynucleotide for expression of that cassette encodes the relevant translation product. Thus, for example, an "iNOS expression cassette" comprises a polynucleotide for expression encoding iNOS operably linked to a promoter.

A graft is any free tissue or organ for transplantation.

GTPCH denotes GTP cyclohydrolase I, which is the rate-limiting enzyme required for $BH_4$ synthesis.

iNOS includes inducible nitric oxide synthase, or any other protein having substantially the same kinetic profile as natural iNOS in catalyzing the formation of NO, utilizing arginine as a substrate, and without requiring elevated intracellular calcium concentration.

A polynucleotide comprises any portion of a nucleic acid molecule which is identified by a specific sequence of nucleotides.

A patient is any animal having a wound or in need of transplantation of a graft.

A product of iNOS refers to NO as well as any other end product or intermediate product of iNOS catalysis, such as N-hydroxyarginine.

A promoter is a polynucleotide required for transcription at appreciable levels of a second polynucleotide to which it is operably linked.

A vector is any polynucleotide competent for introducing one or more exogenous nucleic acid sequences into a cellular environment.

A wound is any trauma to the tissue of a patient resulting in interruption of continuity within the tissue.

2. Methods of iNOS Therapy

The present inventive methods comprise supplying exogenous iNOS to cells associated with a region of interest, e.g., in the region of the graft or the wound. iNOS can be supplied in any manner sufficient to produce biologically active products of iNOS-mediated catalysis in the region of interest. Many appropriate methods are disclosed in International Patent Application No. WO 96/00006, (Billiar et al.)).

3. ISOLATED OR PURIFIED iNOS OR $BH_4$

Some applications of the present inventive methods involve treatment of the surface of a patient, i.e., treatment of a surface wound. In some embodiments, iNOS is administered to the tissue of interest in the form of isolated iNOS protein. Isolated iNOS can be obtained either by purifying it from tissue or cultured cells. Additionally, isolated iNOS can be obtained from expressing a recombinant iNOS expression cassette in a suitable cell.

iNOS can be applied to the surface tissue in any manner appropriate to increase the concentration of biologically active products of iNOS catalysis. Thus, for example, isolated or purified iNOS protein can be included in a liquid solution or gel or salve which is applied to the tissue. Preferred solutions are neutral physiological saline solutions, and can contain other pharmacologically active agents as well. Preferably, the solution contains factors essential for iNOS function, such as flavin adenine dinucleotide (FAD), flavin mononucleotide (FMN), and nicotinamide adenine dinucleotide (NADPH); most preferably the solution contains arginine and $EH_4$.

The solution comprising iNOS can remain in contact with the tissue for a length of time appropriate for imparting the desired therapeutic benefits. Thus, for example, for treating a large wound, the solution can remain in contact with the wound tissue until the wound is substantially closed. The desired length of time during which the solution is in contact with the tissue will depend to a large extent upon the size and location of the tissue.

Transfer of exogenous iNOS to the tissue of interest results in iNOS catalysis and the resultant production of biologically active compounds such as NO and N-hydroxyarginine.

The co-transfer of $BH_4$ optimizes iNOS catalytic activity in the region of interest. Where the method further comprises administration of $BH_4$ to the tissue, this cofactor can also be supplied topically in a like manner. Where iNOS and $BH_4$ are supplied topically, both of them are preferably in the same solution. $BH_4$ is suitably applied in concentrations ranging from about 1 $\mu$M to about 10 mM, preferably from about 10 $\mu$M to about 1 mM, and more preferably from about 100 $\mu$M to about 900 $\mu$M (such as, for example, from about 250 $\mu$M to about 750 $\mu$M, or from about 400 $\mu$M to about 600 $\mu$M, i.e., about 500 $\mu$M).

4. Expression Cassette Transfer

A preferred method of supplying exogenous iNOS or $BH_4$ is by transferring a vector comprising an expression cassette to cells associated with the region of interest such that the cells express iNOS and produce a biologically active product of iNOS catalysis in the region and/or express GTP cyclohydrolase I (GTPCH, and produce $BH_4$.

A. Expression Cassettes

Expression cassettes employed in the present inventive methods, such as iNOS expression cassettes or GTPCH expression cassettes, are of any type appropriate for cells containing the cassette to express the protein of interest. Thus, for example, an expression cassette comprises a polynucleotide encoding iNOS or GTPCH operably linked to a promoter.

Any promoter and/or enhancer sequence appropriate for controlling expression of polynucleotides from the vector can be used in constructing an expression cassette according to the present inventive method. While such promoters/enchanter elements are well known in the art, examples of suitable promoters include prokaryotic promoters or viral promoters, (e.g., ITRs, or LTRs; immediate early viral promoters, such as herpesvirus IE promoters, or cytomegalovirus (CMV) IE promoters; or other viral promoters, such as Rous Sarcoma Virus (RSV) promoters, or Murine Leukemia Virus (MLV) promoters). Other suitable promoters are eukaryotic promoters, such as constitutively active promoters (e.g., the β-actin promoter), signal specific promoters (e.g., inducible promoters, such as a promoter responsive to TNF), or tissue-specific promoters, (e.g., those active in epidermal tissue, dermal tissue, tissue of the digestive organs (e.g., cells of the esophagus, stomach, intestines, colon, etc., or their related glands), smooth muscles, such as vascular smooth muscles, cardiac muscles, skeletal muscles, lung tissue, hepatocytes, lymphocytes, endothelial cells, sclerocytes, kidney cells, glandular cells (e.g., those in the thymus, ovaries, testicles, pancreas, adrenals, pituitary, etc.), tumor cells, cells in connective tissue, cells in the central nervous system (e.g., neurons, neuralgia, etc.), cells in the peripheral nervous system, or other cells of interest.

Which promoter is used in a given expression cassette will depend, in part, on the choice of vector. Thus, for example, an expression cassette can comprise a native retroviral LTR promoter operably linked to a coding polynucleotide when the vector is a retroviral vector.

In addition to a promoter, an expression cassette for use in the present inventive methods comprises a polynucleotide encoding a protein of interest. Preferably, the polynucleotide is a synthetic DNA, cDNA or genomic DNA fragment encoding a protein which exhibits functional iNOS catalytic activity. More preferably, the polynucleotide encodes iNOS, such as human hepatocyte iNOS or other iNOS. In other embodiments, an expression cassette comprises a polynucleotide, such as, for example, a synthetic DNA, cDNA or genomic DNA fragment, encoding a protein which exhibits functional GTPCH catalytic activity. More preferably, the polynucleotide encodes GTPCH. Expression cassettes can comprise other polynucleotides, such as a polyadenylation sequence. Also, expression cassettes can encode more than one protein.

In some embodiments, iNOS and/or GTPCH expression cassettes are both transferred to cells associated with the region of interest. The iNOS expression cassette and GTPCH expression cassette can be co-transferred or transferred separately. When transferred separately, the iNOS expression cassette and the GTPCH expression cassette can be transferred to the same cells, or to different cells associated with the region of interest. More preferably, the iNOS expression cassette and the GTPCH expression cassette are co-transferred, such as being contained within the same vector. More preferably, the iNOS expression cassette and GTPCH expression cassette are the same cassette. For example, an expression cassette can comprise a sequence encoding iNOS and a sequence encoding GTPCH separated by ribosome entry sites.

B. Vectors

An expression cassette for use in the present inventive methods such as those described supra is contained within a vector. Of course, in addition to an iNOS expression cassettes or a GTPCH expression cassette, the vector can also include other expression cassettes, such as, for example, cassettes for expressing a selectable marker (e.g., β-gal or a marker conferring resistance to a toxin), a pharmacologically active protein, a transcription factor, or other biologically active substance.

Any vector appropriate for transferring an exogenous expression cassette to a cell is included within the scope of the present inventive methods. Preferably, the vector is a viral vector. Examples of viral vectors employed in accordance with the present inventive method include, but are not limited to, retroviral vectors, adenoviral vectors, adeno-associated viral vectors, herpesviral vectors, SV40 viral vectors, polyoma virus vectors, pappiloma virus vectors, picnoravirus vectors, vaccinia virus vectors, or other suitable vectors.

Preferred retroviral vectors are derivatives of Moloney murine leukemia virus (MoMLV). A preferred retroviral vector for use in the present inventive method is MFG, such as MFG-iNOS or DFG-iNOS-neo, described in Examples 1.C and 1.D, respectively. A preferred adenovirus for use in the present inventive methods is Ad-iNOS or Ad-GTPCH, such as described in Examples 1.E. and 1.F, respectively.

In addition to viral vectors, any non-viral vector capable of expression upon infection of target cells can be used in the present inventive methods. Preferably, a non-viral vector is a plasmid. A preferred plasmid vector for use in the present inventive methods is pCIS, such as, for example, pCIS-iNOS or pCIS-GTPCH, as described in Examples 1.A and 1.B, respectively.

The skilled artisan will be able to incorporate an expression cassette into the nucleic acid sequence of the vector. Methods for incorporating expression cassettes into viral vectors are well known in the art (see e.g., Sambrook, et al. *Molecular Cloning: a Laboratory Manual,* 2d edition, Cold Spring Harbor Press (1989)) and include direct cloning, site specific recombination using recombinases, such as the flp recombinase or the cre-lox recombinase system (reviewed in Kilby et al. *Trends in Genetics,* 9, 413–21 (1993)), homologous recombination, and other suitable methods of constructing a recombinant vector.

C. Target Cells

The present inventive methods comprise transferring an expression cassette to cells associated with the region of interest (i.e., a wound or a graft). Any suitable cells associated with the region of interest which are capable of supporting expression of the coding polynucleotide of the cassette are encompassed within the present inventive methods. Such cells can be cells in situ, such as cells of the graft tissue or of the wound tissue, or they can be cells in vitro.

Preferably, the cells associated with the region of interest are cells in situ. Thus, iNOS or $BH_4$ can be supplied exogenously to the region of interest by cells indigenous to that tissue. The transfer of an iNOS expression cassettes to cells of the tissue at interest results in those cells expressing iNOS. iNOS activity in the region of interest increases the local concentration of iNOS catalytic products. Transfer of a GTPCH expression cassette results in expression of GTPCH within the cells, and the production of $BH_4$ to the region of interest, optimizing iNOS activity within the region.

In other embodiments, the cells associated with the region of interest are cells in vitro, such as cells in primary culture. Preferably, the cells are cells appropriate for the tissue-type of interest. For example, to populate a vascular lumen, the cells are preferably endothelial cells or vascular smooth muscle cells. A direct source of these vascular cells can be obtained, for example, by harvesting a portion of a saphenous vein or any other accessible vein or artery from the patient. Methods for primary cell culture are well known in the art.

Following transfer of the vector comprising the expression cassette to the cells in vitro, the cells associated with the region are transferred to the region of interest. Transfer of cells in vitro to a region of interest is accomplished by known means. For example, cells can be transferred to internal tissue of a patient by methods described herein. Further methods of transferring cells containing an expression cassette are described in International Patent Application No. WO 96/00006, (Billiar et al.)).

Thus, iNOS or $BH_4$ can be supplied exogenously to the region of interest by cells not indigenous to that tissue. Thereupon, the exogenous iNOS-producing cells populate the region and produce iNOS. iNOS activity in the region of interest increases the local concentration of iNOS catalytic products. Similarly, exogenous GTPCH-producing cells populate the region and produce $BH_4$.

5. Vector Transfer

The present inventive methods comprise transferring a vector comprising an expression cassette, such as those described herein, to cells associated with the region of interest (e.g., a wound or a graft). Any method of transferring the expression cassette to the cells is appropriate so long as a product of the expression cassette is produced in the cells. These methods apply equally to transfer of vectors comprising iNOS expression cassettes as well as GTPCH expression cassettes.

A. Non-Viral Vectors

Any means of introducing non-viral vectors into target cells, such as by direct DNA injection, electroporation, calcium-phosphate mediated cell transfection, lipofectamine, DAEA-dextran-mediated cell transfection, polybrene-mediated delivery, host cell fusion, microinjection, and polylysine-mediated cell transfection is appropriate within the present inventive context. Such methods are well known in the art, and some are described in International Patent Application No. WO 96/00006, (Billiar et al.)). A preferred method of transferring the expression cassette within a nonviral vector, such as a plasmid, is via liposome-mediated transfection of the target cells, such as endothelial cells, in vitro or in situ. If the vector is transfected in vitro, the cells associated with the region of interest are subsequently transferred to the patient.

B. Viral Vectors

Transfer of an expression cassette to cells associated with the region of interest where the cassette is within a viral vector is accomplished by infecting the cells with the virus. Where the virus is a retrovirus, such as MFG-iNOS or DFG-iNOS-Neo, described in Examples 1.C and 1.D, the virus can be first transfected into an appropriate packaging cell line for generation of infectious virus, for example, as described in Example 1.H. Cells associated with the region of interest can be infected in vitro or in situ. Moreover, the mode of transfer of the expression cassette does not depend on the identity of the coding polynucleotide.

C. In Vitro Delivery

Infectious viruses are used to infect cultured cells in vitro. The precise method for infecting target cells in vitro will depend upon the viral vector used; however, such methods are well known in the art. Some suitable methods are described in International Patent Application No. WO 96/00006, (Billiar et al.)).

D. In situ Delivery

Some applications of the present inventive methods involve transfer of expression cassettes in situ. In situ transfer can be either in vivo (i.e., to a wound or to a graft following implantation), or ex vivo (i.e., to a graft prior to implantation). Any method of delivering the vector comprising the expression cassette to cells associated with the region of interest in situ is within the present inventive methods. Such methods also apply to transfer of exogenous cells to the region of interest. Methods for in situ delivery of vectors preferably involve physically segregating the region of interest from the remainder of the patient's tissue in order to properly target the vector within the region. Upon segregation, the vector is applied to the region of interest in a manner appropriate to transfer the expression cassette into the cells associated with the region of interest.

For applications in which the region of interest is external, such as a surface wound, the vector preferably is applied to the tissue comprising the wound in a carrier appropriate for transferring the vector, such as ointment, cream, lotion, colloidal dispersion such as a gel or magma or any other acceptable carrier. Preferred carriers are neutral physiological saline solutions, and can contain other pharmacologically active agents as well. Thus, for example, a solution for transferring a vector can comprise a nutrient-rich medium (e.g., culture medium), or neutral saline or other appropriate composition. For viral vectors, the carrier can contain agents that stabilize viral titer (e.g., glycerol). External wounds are already partially isolated from the rest of the patient's tissue by virtue of anatomy. The vectors desirably are further isolated by being retained in place relative to the wound by an appropriate wound dressing, such as a plastic film covering the wound.

Tissue ex vivo, such as, for example, a graft, is completely isolated from the patient. For ex vivo vector transfer, the vector can be applied to the tissue in any suitable manner, e.g., in a carrier appropriate for transferring the vector. For example, the tissue can be incubated in a carrier containing the vector particles by any suitable incubation method. Other tissue can be perfused with the solution containing the vector.

The vectors or exogenous cells preferably remain in contact with the wound or tissue for a period of time sufficient to promote the transfer. For example, a carrier comprising a vector will remain in contact with the wound or ex vivo tissue from about one minute to about 2 hours, more preferably between 10 minutes and an hour, and most preferably from about 20 minutes to 40 minutes. In many applications, the carrier will optimally remain in contact with the wound or tissue for about 30 minutes.

E. Internal Delivery

For in situ delivery of a vector internally, the region of interest desirably is further segregated from the remainder of the patient's tissue. Any of a variety of known surgical procedures for physically segregating the region of interest is appropriate. Various endovascular surgical techniques appropriate for segregating a region of interest are available, depending upon the location of the target.

Endovascular surgical procedures include, but are not limited to, balloon angioplasty, intravascular stents, laser-assisted balloon angioplasty, double balloon catheterization, mechanical endarterectomy and vascular endoscopy. For a review of endovascular alternatives, see generally Ahn, "Endovascular Surgery," in *Vascular Surgery, A Comprehensive Review*, Ed. W. S. Moore, W. B. Saunders & Co., Philadelphia (1993)).

Several catheter designs can be utilized for local delivery of an iNOS or iNOS/GTPCH containing entity to the patient. One catheter design consists of two independently inflated balloons, one proximal and one distal to the vascular delivery site. Inflation of these balloons provides an evacuated isolated arterial segment into which vectors for expression cassette delivery can be infused. This system is, however, limited by a failure to provide distal arterial perfusion. A second catheter design developed by Wolinsky allows the infusion of the iNOS containing carrier through 25–100 $\mu$M pores under pressures up to 5 atm. This perfusion pressure increases the depth of penetration by the iNOS vectors and additionally increases expression cassette transfer efficiency. Yet another catheter design utilizes an expandable stent which traps the balloon against the arterial wall and allows intramural delivery of the expression cassette through spaces in the stent material. Additionally, these stents can be modified with burrs which create holes deeper in the vessel wall and allow flow of the expression cassette delivery agents to these sites to allow more uniform delivery of the expression cassette throughout the vessel wall.

Another delivery mechanism is to coat the catheter with a hydrophilic polyacrylic acid polymer which acts as a drug-absorbing sponge. By disrupting the vessel during the angioplasty procedure, this hydrogel is deposited within the vessel wall and will allow sustained delivery of the vector at the arterial wound site. Additionally, the iontophoretic balloon catheter is a catheter design which uses low electrical current to change the cell membrane polarity and allow the diffusion of charged DNA particles into the cell. This is a potential delivery mechanism for plasmid DNA expression cassette constructs. Also, biodegradable stents formed from agents such an ethylenevinyl acetic copolymer are appropriate for localized delivery to vascular tissue. Alternatively, an intravascular stent can be utilized wherein the endovascular scaffold of the stent is bathed in a ointment, cream, lotion, colloidal dispersion such as a gel or magma or any other acceptable carrier which comprises the iNOS containing entity (or a GTPCH containing entity) for delivery to the targeted portion of a vessel segment. This solution is applicable to either an in situ or ex vivo based vessel delivery.

Another specific application, offered for the purpose of example and not of limitation, is the use of a self-expanding stent. This intravascular stent can be bathed in a gel solution comprising an iNOS and/or GTPCH containing recombinant viral supernatant and delivered percutaneously to the target vessel site. An initial angioplasty, if necessary, is followed by delivery of the bathed scaffold to the target vessel site. The delivery catheter is removed and the scaffold is dilated with a conventional balloon. It is within the purview of the skilled vascular surgeon to use other types of intravascular stents such as a balloon expandable stent or a thermal expanding stent. Additionally, numerous balloon catheters of varying sizes, shapes, and types are available to the skilled vascular surgeon for endovascular delivery of the iNOS or iNOS-GTPCH composition.

The present inventive method can be employed in connection with surgical procedures to bypass a vascular occlusion. Such procedures typically involve a homograft or heterograft comprising an artery or vein, or a segment thereof, or an artificial conduit. Vascular bypass procedures involve forming a proximal and distal anastomosis between the graft conduit and the vessel. An iNOS expression cassette can be transferred to the cells in the region of the anastomoses to promote proper healing of the surgical wound between the two conduits. Where the graft conduit is not artificial (e.g., an artery, a vein, or a segment thereof), an iNOS expression cassette can be transferred to the cells of the graft lumen. iNOS can also be transferred to the graft region by seeding the graft with cells into which iNOS expression cassettes have been introduced in vitro. Additional preferred methods for delivering an expression cassette to a vessel in vivo or ex vivo involve vascular surgery, such as those surgical procedures characterized in the International Patent Application No. WO 96/00006, (Billiar et al.)).

6. iNOS Therapy to Promote Wound Healing

In one embodiment, the present invention provides a method of promoting the closure (i.e., healing) of a wound in a patient. This method involves transferring exogenous iNOS to the region of the wound whereby a product of iNOS is produced in the region of the wound to promote the closure (i.e., healing) of the wound.

The present inventive method promotes closure (i.e., healing) of both external (e.g., surface) and internal wounds. Wounds to which the present inventive method is useful in promoting closure (e.g., healing) include, but are not limited to, abrasions, avulsions, blowing wounds, burn wounds, contusions, gunshot wounds, incised wounds, open wounds, penetrating wounds, perforating wounds, puncture wounds, seton wounds, stab wounds, surgical wounds, subcutaneous wounds, tangential wounds, or traumatopneic wounds. Preferably, the present inventive methods are employed to close chronic open wounds, such as non-healing external ulcers and the like.

Exogenous iNOS can be introduced into the region of the wound by any appropriate means, such as, for example, those means described herein. For example, where the wound is a surface wound, iNOS can be supplied exogenously by topical administration of iNOS protein to the region of the wound.

Preferably, exogenous iNOS is provided to the wound by transferring a vector comprising an iNOS expression cassette to cells associated with the wound. Upon expression of iNOS within the cells in the region of the wound, a product of iNOS is produced to promote wound closure (i.e., healing). Transferring a vector comprising an iNOS expression cassette to cells associated with the wound is preferred as such procedure is minimally invasive, supplies iNOS products locally within the region of the wound, and requires no reapplication of salves, solutions, or other extrinsic media. Furthermore, iNOS activity remains expressed during wound closure and will inactivate following healing.

The vector comprising the iNOS expression cassette can be transferred to the cells associated with the wound in any manner appropriate to transfer the specific vector type to the cells, such as those methods discussed herein.

As discussed above, the cells associated with the wound to which the vector is transferred are any cells sufficiently connected with the wound such that expression of iNOS within those cells promotes wound closure (i.e., healing), such as cells within the wound or cells from other sources. In one embodiment, the cells are cells of the wound, and the present inventive method comprises transfer of the vector to the cells in situ.

In other embodiments, the cells are not the cells of the wound, but can be cells in an exogenous tissue, such as a graft, or can be cells in vitro. For example, to promote the healing of certain types of wounds, the cells associated with the wound can be cells within a graft, such as a skin graft. Transfer of the vector to the cells associated with the wound, thus, involves transferring the vector to the cells within the graft ex vivo. For other wounds, the cells associated with the wound are cells in vitro, and the cells are transferred to the region of the wound following transfer to them of a vector containing the iNOS expression cassette.

The present inventive method applies to any patient having a wound. For example, the patient can be any animal, such as a mammal. Preferably, the patient is human. The present inventive method of promoting closure (i.e., healing) of wounds is most preferably employed in patients deficient for NO production, such as patients suffering from diseases or conditions of the type discussed above. Thus, for example, transfer of iNOS to the regions of wounds in patients deficient for NO production permits the wounds to close or heal at a pace at least commensurate with that observed in patients not suffering from NO deficiencies, as demonstrated, for instance, in Example 3.

While in many applications transfer of iNOS to cells associated with the wounds is sufficient, in other embodiments iNOS enzymatic activity desirably is further enhanced. A preferred means of enhancing iNOS activity is by exogenous $BH_4$, for example as indicated by Tzeng et al., Surgery, 120(2), 315–21 (1996). Exogenous iNOS can be introduced into the region of the wound by any appropriate means, such as those means described herein. For example, where the wound is a surface wound, $BH_4$ can be supplied exogenously by topical administration of isolated or purified $BH_4$ to the region of the wound.

In other embodiments, exogenous $BH_4$ is supplied to the region of the wound by transferring a vector containing an expression cassette to cells associated with the wound such that the cells produce $BH_4$. A preferred expression cassette is a GTPCH expression cassette. iNOS and/or $BH_4$ can be supplied in the same or different manners. Thus, for example, iNOS can be supplied topically while $BH_4$ is supplied by transfer of a GTPCH expression cassette; conversely, exogenous iNOS can be supplied by transfer of an iNOS expression cassette and $BH_4$ supplied topically. Exogenous iNOS and $BH_4$ can both be supplied topically or both be supplied by expression cassette transfer.

Preferably, both iNOS and $BH_4$ are provided to the region of the wound by transfer of appropriate expression cassettes to cells associated with the wound. For example, in one embodiment, the iNOS expression cassette and the GTPCH expression cassette are co-transferred. Where the iNOS expression cassette and the GTPCH expression cassette are co-transferred, they can be within separate vectors. Preferably, however, the co-transferred iNOS expression cassette and the GTPCH expression cassette are within the same vector. Most preferably, the co-transferred iNOS expression cassette and the GTPCH expression cassette comprise a single expression cassette, such as an expression cassette in which their respective coding polynucleotides are separated by ribosome entry sites. Such co-transfer will ensure expression of both iNOS and $BH_4$ with similar kinetics and identical tissue distribution. Alternatively, the expression cassettes can be within different vectors and either transferred to cells together or not co-transferred, as discussed herein.

7. iNOS Expression Cassette Transfer Therapy to Reduce Graft Rejection

In another embodiment, the present invention provides a method of transplanting a graft into a patient. The method involves transferring a vector comprising an iNOS expression cassette to cells associated with the graft and surgically incorporating the graft tissue into the patient. Upon expression of iNOS within the patient, a product of iNOS is produced in the region of the graft to attenuate vasculopathy in the region of the graft.

Surgical procedures for implanting a graft within a patient are within the ordinary skill in the art. Such vary widely according to the tissue type and other parameters. Preferably, such procedures involve forming at least one anastomosis between the graft tissue and the vasculature of the patient. The present invention embraces any manner of surgical procedure for implanting a graft into a patient appropriate for the graft to survive within the patient.

In accordance with the method of the present invention, iNOS acts to reduce or eliminate vasculopathy associated with graft implantation or transplantation. Preferably, products of iNOS catalytic activity attenuate vasculopathy by inhibiting neointimal hyperplasia and/or cicatrization. Thus, for example, NO, N-hydroxyarginine, and other byproducts of iNOS enzymatic activity act to prevent vascular occlusion by inhibiting proliferation of smooth muscle cells within vascular lumens, as described, for instance, in Example 4.

The present inventive method involves transferring an iNOS expression cassette, such as those described herein, to cells associated with the graft. As indicated above, any cells associated with the graft are appropriate targets for transfer of the iNOS expression cassette. In one embodiment, the cells associated with the graft, such as demonstrated, for instance, in example 4, are cells within the tissue comprising the graft. In a second embodiment, the cells associated with the graft are cells of the patient in the region of the graft (e.g., in the region of an anastomosis). In yet another embodiment, the cells associated with the graft are neither cells of the graft itself nor of the patient. Thus, for example, the cells associated with the graft can be cells in vitro which are transferred to the region of the graft after the vector containing the iNOS expression cassette is transferred to them, as indicated above.

The present inventive method employs a vector to deliver the iNOS expression cassette to the cells associated with the graft. Any vector appropriate for delivery of an expression cassette to target cells is within the scope of the present inventive method, such as, for example, those vectors described above.

The present inventive method is appropriate for any type of tissue graft. The graft can be an allograft, such as an autograft or a homograft; alternatively, the graft can be a heterograft, such as a xenograft.

In preferred embodiments, the graft comprises vasculature, such as, for example a graft comprising arterial tissue, venous tissue, or cardiac tissue. Thus, for example, transfer of an iNOS expression cassette to cells associated with an aortic graft facilitates transplantation of an aorta, or a section thereof, into a patient by attenuating vasculopathy in the region of the graft. Similarly, transfer of an iNOS expression cassette to cells associated with a cardiac graft, such as in connection with a heart transplant procedure or in connection with a procedure to engraft a cardiac valve, facilitates transplantation of the graft into a patient by attenuating intimal hyperplasia and/or cicatrization in the region of the graft.

In other preferred embodiments, the graft is not vascular tissue, but is vascularized. For example, the graft can be hepatic tissue, such as a complete liver or part of a liver, renal tissue, pulmonary tissue, or other such tissue. Furthermore, the graft employed in accordance with the present inventive method can comprise a combination of tissue types. Thus, for example, a graft in accordance with the present inventive method can comprise a complete heart-lung combination. In further embodiments, the graft comprises dermal tissue, such as a skin graft.

Preferably, in addition to transferring an iNOS expression cassette, the present inventive method comprises transferring a vector comprising a GTPCH expression cassette to cells associated with the graft.

In one embodiment, the iNOS expression cassette and the GTPCH expression cassette are co-transferred. Where the iNOS expression cassette and the GTPCH expression cassette are co-transferred, they need not be within the same vector. Preferably, however, the co-transferred iNOS expression cassette and the GTPCH expression cassette are within the same vector. Most preferably, the co-transferred iNOS expression cassette and the GTPCH expression cassette comprise a single expression cassette, such as an expression cassette in which their respective coding polynucleotides are separated by ribosome entry sites. Alternatively, the expression cassettes can be within different vectors and either transferred to cells together or not co-transferred.

The vector comprising the iNOS expression cassette can be transferred to the graft tissue at any time relative to engrafting. Thus, in one embodiment, the vector is transferred to the region of the graft prior to surgically incorporating the graft tissue into the patient. For example, the graft tissue can be incubated in or perfused with a solution containing the vector prior surgically incorporating the graft into the patient. The period of incubation or perfusion, and composition of the solution, are such that they effect the transfer of the vector containing the expression cassette to the cells, such as those described above.

In other embodiments, the vector is transferred to the region of the graft subsequent to surgically incorporating the graft tissue into the patient. Thus, engrafted tissue can be targeted for delivery of the vector following incorporation of the graft tissue into the patient. Any of the methods described above for in situ delivery of vectors is appropriate for delivery of a vector containing an expression cassette.

The present inventive method applies to any patient into which a graft is to be incorporated. For example, the patient can be any animal, such as a mammal. Preferably, the patient is human.

8. Combined Effects

In preferred applications, transfer of iNOS expression cassettes will produce combined and potentially synergistic effects. Thus, for example, transfer of a vector containing an iNOS expression cassette to a patient undergoing a transplant operation, or to the graft, results in expression of iNOS in cells within the region of the graft. iNOS expression results in topical increases in the concentration of products of iNOS catalysis. These products facilitate a variety of therapeutic effects. For example, the iNOS products promote the healing of the surgical wound (e.g., the suture) between the graft and the patient's tissue in the region of the graft. Additionally, the iNOS products reduce the likelihood of rejection of the graft itself by attenuating neointimal hyperplasia and/or cicatrization, thereby preventing vasculopathy and chronic rejection of the graft tissue.

EXAMPLES

The following examples further illustrate the present invention but, of course, should not be construed as in any way limiting its scope.

Example 1

Many procedures, such as total RNA extraction, Northern blots, Southern blots, Western blots, PCR (including RT-PCR), vector construction, including direct cloning techniques, are techniques routinely performed by one of ordinary skill in the art (e.g., see generally Sambrook et al., *Molecular Cloning, A Laboratory Manual,* Cold Spring Harbor Laboratory, Cold Spring Harbor, N.Y. (1989); Geller, et al., *Proc. Natl. Acad. Sci. USA* , 90, 522–26 (1993); Towbin et al., *Proc. Natl. Acad. Sci. USA,* 76, 4350 (1979); Brenner et al., *BioTechniques* 7, 1096–1103 (1989). As such, they are not set forth herein. However, examples of vectors for practicing the present inventive methods, as well as information concerning the creation of the models employed in the more detailed studies, are set forth herein.

The following vectors containing expression cassettes were employed in experiments described in Examples 2–4. They represent only a small sampling of the vectors appropriate for use in the present inventive methods. Furthermore, the expression cassettes themselves employed within the vectors represent only some of many possible combinations of promoters and coding sequences as discussed with more particularity above.

A. pCIS-iNOS

An exemplified non-viral vector is pCIS-iNOS, as depicted in FIG. 1A. A roughly 4.1 kb (i.e. bp 47–4145) XbaI-Xba1 iNOS polynucleotide was cloned into the Xba1 site within the pCIS polylinker such that it is operably linked to the CMV enhancer/promoter sequence and to the SV40 polyadenylation sequence of the pCIS vector. Additional polynucleotides, from 5' to 3', include a CMV intron, a polylinker sequence for ligation of the DNA fragment, an SV40 origin of replication, a dihydrofolate reductase (DHFR) cDNA, and a β-lactamase expression cassette for imparting ampicillin resistance.

The iNOS expression cassette, thus, comprises the CMV enhancer/promoter of pCIS operably linked to an iNOS polynucleotide. This expression cassette results in high iNOS activity in transient transfection assays.

B. pCIS-GTPCH

Figure 1B:
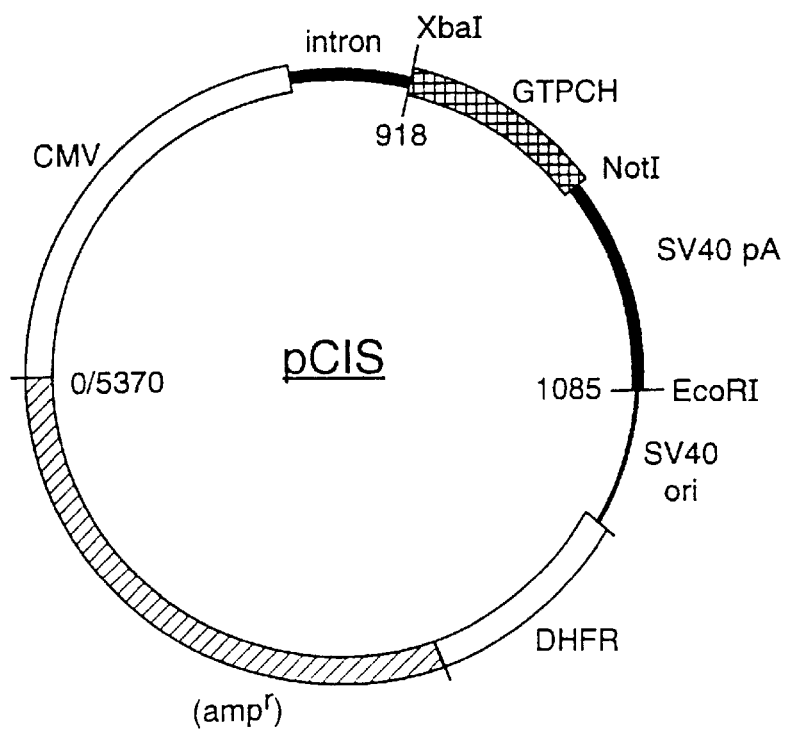

A vector comprising a GTPCH expression cassette is pCIS-GTPCH, as depicted in FIG. 1B. The human GTPCH cDNA was cloned by PCR amplification using primers designed based on the sequence of human GCH-1. (Togari et al., *Biochem. Biophys. Res. Comm.*, 187, 359–65 (1992)). A Xba-NotI fragment encoding GTPCH was subcloned into the pCIS polylinker. The resultant plasmid pCIS-GTPCH was shown to be a functional expression plasmid. The control expression plasmid pIEP-lacZ contains the cDNA for β-galactosidase (provided by P. Robbins, Univ. of Pittsburgh).

The GPTCH expression cassette, thus, comprises the CMV enhancer/promoter of pCIS operably linked to the GPTCH polynucleotide. This expression cassette results in high GPTCH activity in transient transfection assays.

C. MFG-iNOS

Figure 2:
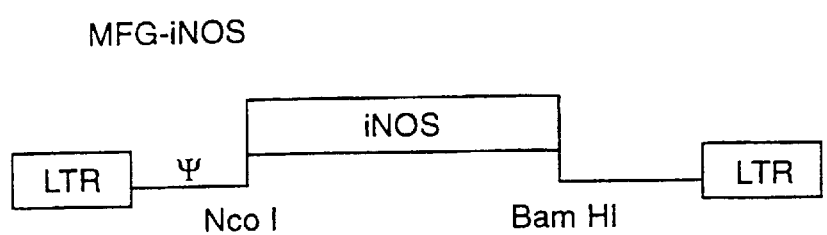
FIG. 2 is a schematic representation of the MFG-iNOS recombinant retroviral vector utilized to exemplify a suitable retroviral vector to transfer an iNOS expression cassette. The IRES fragment allows translation of polycistronic mRNA; LTR indicate the Long Terminal Repeats of the MoMLV virus; iNOS indicates a cDNA encoding human iNOS.

An exemplified retroviral vector is MFG-iNOS, as depicted in FIG. 2. The expression cassette within this vector comprises the viral LTR promoter operably linked to the polynucleotide encoding iNOS.

Figure 3:
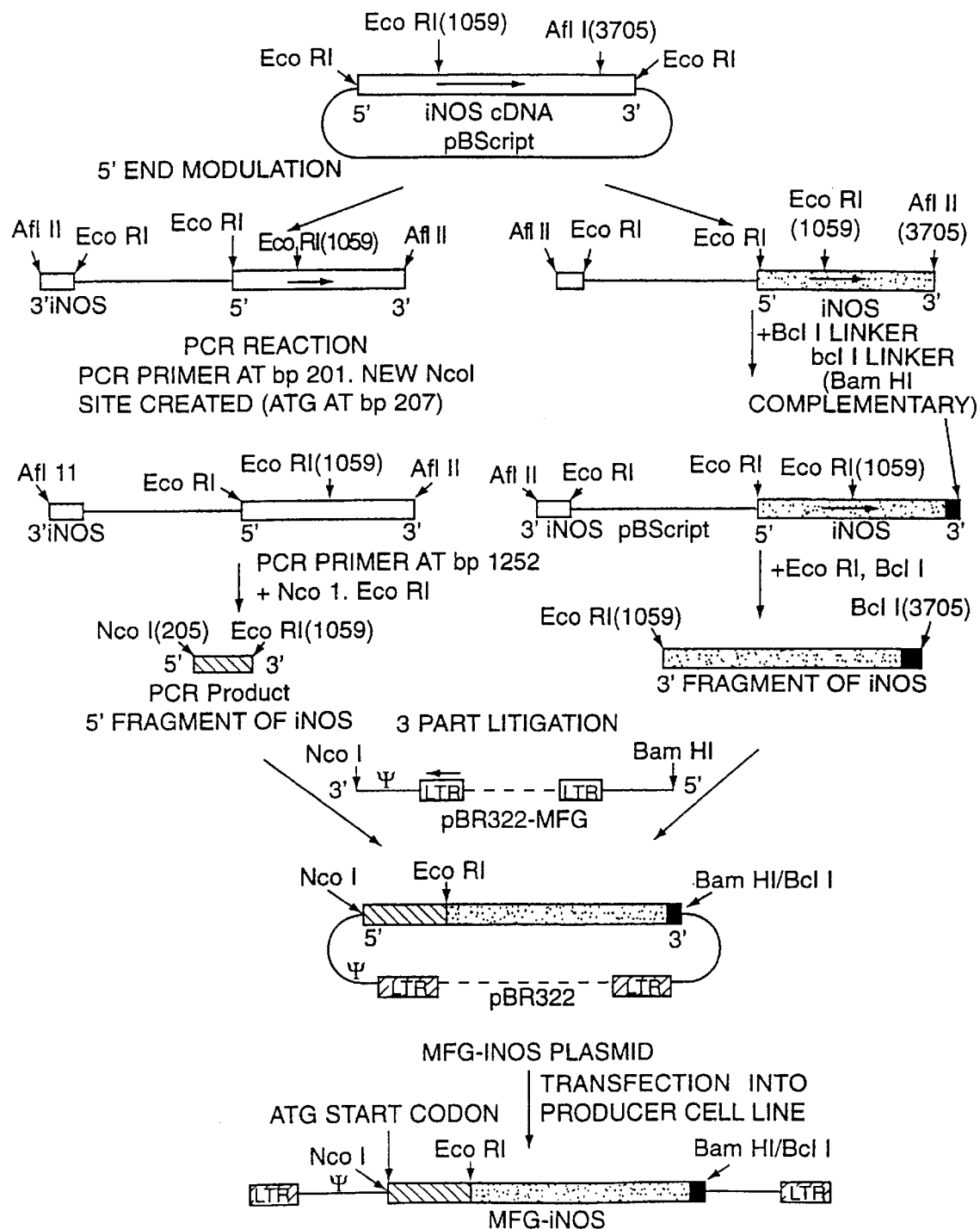
FIG. 3 is a flow diagram depicting the methods utilized to construct the MFG-iNOS recombinant retroviral vector.

As depicted in FIG. 3, MFG-iNOS was constructed using as starting materials the human hepatocyte iNOS cDNA construct and MFG, a simplified MoMVL vector in which the DNA sequences encoding the pol and env proteins have been deleted so as to render it replication defective. The majority of the gag sequence also has been deleted. The expression cassette within this vector, thus, comprises the viral LTR promoter operably linked to the polynucleotide encoding iNOS.

The human hepatocyte iNOS cDNA was inserted into the NcoI and BamHI cloning sites of the retroviral vector MFG. Briefly, the MFG vector has a unique cloning region consisting of a 5' NcoI site and a 3' BamHI site.

PCR primers were used to generate a point mutation at bp 205 of the iNOS cDNA, manufacturing an NcoI site that incorporated the ATG start codon. A 5' fragment of the PCR product of the iNOS cDNA spanning from the NcoI site at bp 205 to the EcoRI site at bp 1059 was isolated. The 3' BamHI site was generated by linearizing the pBScript-iNOS plasmid with AfiII which uniquely cut at bp 3705 of the iNOS cDNA. This restriction site is located approximately 40 bp downstream from the iNOS stop codon. A BclI linker was then ligated to the linearized plasmid. Double digestion with EcoRI and BclI allowed the isolation of a 3' fragment of the iNOS cDNA from bp 1060 (EcoRI) to bp 3710 (BclI). The BclI overhang is complementary to the overhang generated by BamHI. A three part ligation was then performed between MFG, the 5, PCR product with the 5, NcoI site, and the 3' fragment with the 3' BclI linker.

*E. coli* were transformed with the ligation mixture and grown on ampicillin selection medium. Transformants were isolated and screened for the properly reconstituted MFG-iNOS construct. One correct transformant was isolated and a large scale plasmid DNA preparation performed.

Viral supernatants for MFG-iNOS were used to infect endothelial cells in vitro, and iNOS activity was assayed at 48–72 hours after infection to demonstrate that transfer of the expression cassette by this virus could deliver exogenous biologically active iNOS products.

D. DFG-iNOS-neo

Figure 4:
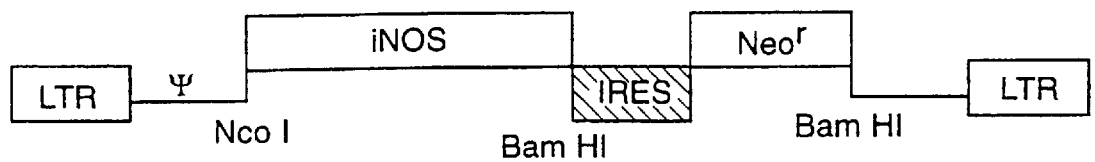
FIG. 4 is a schematic representation of the DFG-iNOS-neo recombinant retroviral vector utilized to exemplify a suitable retroviral vector to transfer an iNOS expression cassette. Neo$^r$ encodes resistance to neomycin; the IRES fragment allows translation of polycistronic mRNA; LTR indicates the Long Terminal Repeat of the MOMLV virus; iNOS indicates a cDNA encoding human iNOS.

This MFG-iNOS containing retroviral construct comprises a selectable neomycin resistance marker (see FIG. 4). The expression cassette within this vector, thus, comprises the viral LTR promoter operably linked to the polynucleotide encoding iNOS.

The MFG retroviral vector had been previously engineered to contain an internal ribosome entry site (IRES) followed by a neomycin resistance expression cassette (Neo$^r$) inserted at the 3' BamHI cloning site of MFG.

Figure 5:
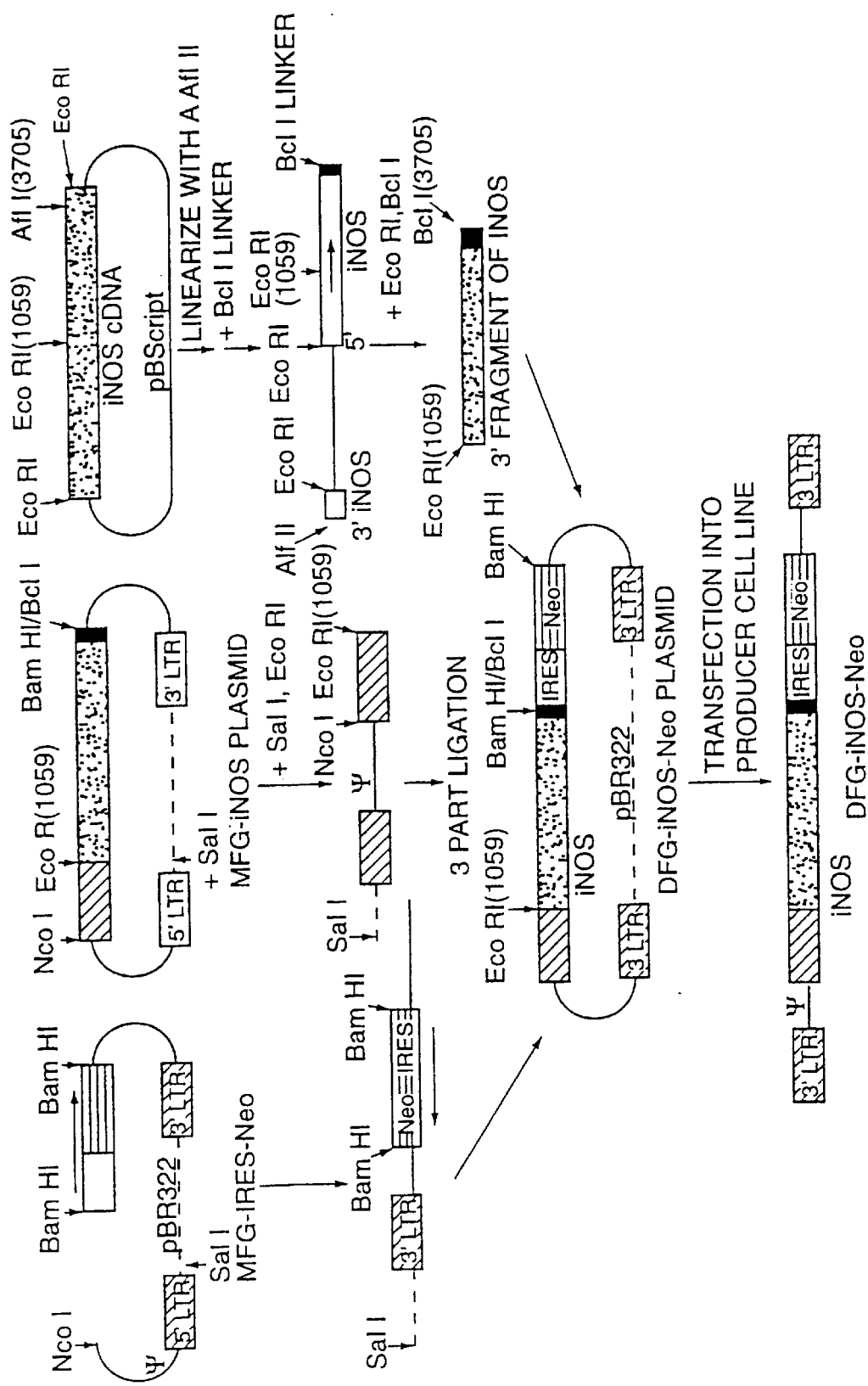
FIG. 5 is a flow diagram depicting the methods utilized to construct the DFG-iNOS-neo recombinant retroviral vector.

The IRES sequence allows for the translation of multiple protein products from a single polycistronic mRNA. As depicted in FIG. 5, this MFGIRES-Neo$^r$ plasmid was digested with the restriction enzymes SalI (which cuts approximately 3000 bps upstream of the NcoI (cloning site of MFG) and BamHI. The larger fragment containing the majority of the MFG backbone attached to IRES and Neo$^r$) was purified. The previously constructed MFG-iNOS vector was also digested with SalI and EcoRl, and a 3.7 Kb fragment containing the 5' portion of the iNOS cDNA was isolated. The 3' end of the iNOS cDNA was the identical 3' fragment with the BclI linker used to construct MFG-iNOS. A 3 part ligation with MFG-IRES-Neo$^r$, 5' SalI-EcoRI fragment containing the 5' end of the iNOS cDNA, and 3' iNOS cDNA with the BclI linker was performed. The ligation mixture was then transformed into *E. coli* and selected for ampicillin resistant transformants. Such a positive transformant with the correctly oriented construct (DFG-iNOS-Neo) was isolated and a large scale plasmid preparation performed.

Viral supernatants for DFG-iNOS-Neo were used to infect endothelial cells in vitro, and iNOS activity was assayed at 48–72 hours after infection to demonstrate that transfer of the expression cassette by this virus could deliver exogenous biologically active iNOS products.

E. Ad-iNOS

An exemplified adenovirus vector containing an iNOS expression cassette is Ad-iNOS. The expression cassette within Ad-iNOS comprises a CMV promoter/enhancer operably linked to a polynucleotide encoding iNOS and the SV40 polyA sequence.

The large size of the adenoviral genome requires that it be separated into two separate plasmids before recombinant manipulations can be performed. The plasmid carrying the 5' portion of the genome was employed for the construction of an adenoviral plasmid carrying the iNOS cDNA. The El region of the adenoviral genome was previously deleted from this plasmid, and, in its place, the full-length iNOS cDNA was inserted along with a CMV enhancer/promoter complex. After this plasmid was generated, it was co-transfected with the plasmid carrying the remainder of the adenoviral genome into 293 cells. These cells constitutively express the El expression cassette product and are therefore able to package infectious adenoviral particles from El deleted constructs.

Following transfection, intracellular recombination generated the full-length adenoviral genome containing the iNOS cDNA. Infectious Ad-iNOS particles were then generated and released from the 293 cells through a lytic process, and the culture supernatant was collected. This supernatant was subjected to sucrose banding to purify and concentrate the Ad-iNOS viral particles. The virus can be stored at −80° C. for extended periods of time.

Ad-iNOS supernatant was tested on a variety of cell types for the ability to infect and transfer iNOS expression to naive cells. These cells include human smooth muscle cells, endothelial cells, and hepatocellular cell lines, as well as rat smooth muscle cells (RSMCs) and primary hepatocytes. All cells were successfully infected with Ad-iNOS with varying levels of efficiency. High levels of iNOS expression and nitric oxide synthesis were detected for all the cells tested, with the greatest nitric oxide synthesis occurring in hepatocytes. These results demonstrated that Ad-iNOS is a functional viral vector that successfully transfers functional iNOS expression cassettes.

F. Ad-GTPCH

An exemplified adenovirus vector containing a GTPCH expression cassette is Ad-GTPCH. The expression cassette within Ad-GTPCH comprises a CMV promoter/enhancer operably linked to a polynucleotide encoding GTPCH. The vector was constructed in a similar manner as Ad-iNOS.

Ad-GTPCH supernatant was tested on a variety of cell types for the ability to infect and transfer GTPCH expression to naive cells. All cells were successfully infected with Ad-GTPCH with varying levels of efficiency, and high levels of GTPCH expression and $BH_4$ were detected for all the cells tested. These results demonstrated that Ad-GTPCH is a functional viral vector that successfully transfers functional GTPCH expression.

G. Control Vectors

The control retroviral vectors MFG-lacZ and Bag-lacZ were previously described (Zitvogel et al., *Human Gene Ther.*, 5, 1493–1506 (1994); Price et al., *Proc. Natl. Acad. Sci. USA*, 84, 156–60 (1987)). Both constructs carry a β-galactosidase expression cassette, while Bag-lacZ additionally carries a Neo expression cassette. The control adenovirus vector Ad-lacZ is similar to the Ad-iNOS iNOS and Ad-GTPCH vectors, except that Ad-lacZ contains a lacZ expression cassette.

H. Production of Replication-Deficient Retrovirus Stock

The retrovirus constructs of Example 1.C. and 1.D were are transfected into the CRIP cell packaging line (Danos and Mulligan, *Proc. Natl. Acad. Sci. USA*, 85, 6460–64 (1988)) using a standard calcium phosphate transfection procedure. The viral vector DFG-iNOS-Neo is capable of imparting resistance to the synthetic antibiotic G418. CRIP cells transfected with DFG-iNOS-Neo were selected on the basis of resistance to G418. The CRIP cell line expresses the three viral proteins required for packaging recombinant viral RNA into infectious particles. Moreover, the viral particles produced by the CRIP cell line are able to efficiently infect a wide variety of species of mammalian cells including human cells. All retroviral particles produced by this cell line are defective for replication but retain the ability to stably integrate into mammalian cells, thereby transferring a heritable trait to these cells. Virus stocks produced by this method are substantially free of contaminating helper-virus particles and are also non-pathogenic.

The DFG-iNOS-Neo plasmid was calcium phosphate transfected into the transient ecotropic packaging cell line BOSC23 (Pear et al., *Proc. Natl. Acad. Sci. USA*, 90, 8392–96 (1993)). Viral supernatants were collected 72 hours after transfection and used to infect CRIP cells (Danos and Mulligan, supra) to generate a stable amphotropic producer cell line. CRIP cells were incubated with BOSC23 viral supernatant with 8 µg/ml polybrene then selected with G418 (750 µg/ml, Geneticin). The BOSC23 supernatant had an estimated titer of $10^5$ PFU/ml. Individual G418-resistant CRIP colonies were isolated and screened for nitrite ($NO_2^-$) production as an indirect measure of iNOS expression. The colonies generating the highest $NO_2^-$ levels were tested for virus production by the number of G418-resistant NIH3T3 colonies following infection with serial dilutions of the CRIP-DFG-iNOS-Neo supernatants. The BAG mobilization assay for replication competent helper virus was performed as previously described (Danos, "Construction of Retroviral Packaging Cell Lines," in, Collins, M. (ed), *Methods in Molecular Biology*, Vol. 5, *Practical Molecular Virology, Viral Vectors for Gene Expression*, Humana Press Inc., Clifton, N.J. pp. 17–27 (1991)).

I. Measurement of $NO_2^-/NO_3^-$ Production

The direct iNOS enzyme assay measures the conversion of [$^3$H]-arginine to [$^3$H]-citrulline, as described (Bredt et al., *Nature*, 351,714–18 (1991)). $NO_2^- + NO_3^-$ levels are measured in the culture supernatants by an automated procedure based on the Griess reaction (Green et al., *Anal. Biochem.*, 126, 131–37 (1982)).

J. Detection of iNOS Expression

To assess whether an iNOS expression cassette functions in a cell to which it has been transferred, RT-PCR is performed on isolated total RNA.

First strand cDNA synthesis is performed on 300 ng of total RNA in a volume of 10 µl with 50 mM Tris-HCl (pH 8.3), 75 mM KCl, 3 mM $MgCl_2$, 1.0 mM dNTPs, 10 mM DL-dithithreitol, 10 units human placental RNAase inhibitor, and 200 units MMLV reverse transcriptase at 37° C. for 60 minutes. cDNAs (100 ng) were combined in 50 µl in 10 mM Tris-HCl (pH 8.3), 50 mM KCl, 200 µM dNTP, 1.5 mM $MgCl_2$, 100 pM each PCR primer, and 1.25 units Taq DNA polymerase, and PCR amplification was carried out with denaturation at 94° C. for 1 minute., annealing at 57° C. for 2 minutes, and elongation at 72° C. for 3 minutes for 40 cycles.

The iNOS oligonucleotide primers specifically recognize the human hepatocyte iNOS cDNA sequence and do not detect rodent sequences. The 18 bp 5' primer spans from bp 3376–3393 of the iNOS cDNA, and the 18 bp 3' primer spanned from bp 3674–3691 of the iNOS cDNA as set forth in U.S. Pat. No. 5,468,630, issued to Billiar et al. on Nov. 21, 1995. The predicted PCR product is 316 bps. RT PCR for β-actin message serves as a control. The β-actin PCR product measures 652 bps.

K. Source of Knockout Mice

A mouse strain lacking a functional iNOS gene (the iNOS Knockout or KO mouse) mouse has been described (MacMicking et al., *Cell*, 81, 641–50 (1995)). This strain was used for experiments described in Experiment 4.

L. Statistical Analysis

Values for $NO_2^-$, $NO_2^- + NO_3^-$, cGMP in Table 1, and myointimal thickness are expressed as means±standard deviation (SD). The significance of differences was determined using the ANOVA test. Statistical significance was established at a p value<0.01.

Values for GTPCH activity in Table 2, intracellular biopterin levels, and $NO_2^-$ are expressed as means±SEM. The significance of differences for GTPCH activity and biopterin levels was determined using the paired t-test with statistical significance at a p value of<0.05. The statistical analysis of $NO_2^-$ levels was determined using the standard ANOVA test. Statistical significance was established at a p value<0.01.

Values for wound closure rates in Table 3 are expressed as means±SEM. The significance of differences for KO mouse wound closure vs. WT groups and KO+Ad-iNOS was determined using the ANOVA test with statistical significance at a p value of<0.001. The statistical analysis of KO+Ad-lacZ mouse wound closure was determined using the ANOVA test with statistical significance at a p value<0.01.

Example 2

The experiments described in this Example demonstrate that iNOS activity is enhanced through supplying exogenous $BH_4$.

Initial experiments demonstrated that a GTPCH expression cassette can be transferred to cells in vitro and expressed. Furthermore, iNOS activity was observed to require a source of exogenous $BH_4$, and transfer of a GTPCH expression cassette, even at low efficiency, was as effective as transferring purified $BH_4$. Supply of exogenous $BH_4$ to the cell culture was demonstrated not to require transfer of the expression cassette to every cell, or to require direct contact between transfected cells and untransfected cells. Thus, only a few cells expressing GTPCH and synthesizing the cofactor can optimally support iNOS activity in a large population of cells.

Culture of NIH-3T3 Cells

NIH3T3 cells were cultured as described (Tzeng et al., *Sugery*, 120(2), 315–21 (1996)). Rat aortic smooth muscle cells were cultured from thoracic aorta explants as described (Davies et al., *J. Cell. Physiol.*, 159, 399–406 (1994)) and used between passages 2–8 as described (Tzeng et al., *Sugery*, 120(2), 315–21 (1996)).

3T3-iNOS are NIH3T3 engineered to stably express human iNOS as previously described (Tzeng et al., *Proc. Natl. Acad. Sci. USA*, 92, 11771–75 (1995)). NIH3T3 cells were infected with the DFG-iNOS retrovirus and then were selected in the synthetic neomycin G418 to yield a population of cells expressing human iNOS. 3T3 cells lack GTPCH activity and are $BH_4$ deficient. Abundant levels of iNOS protein are expressed in these cells but NO synthesis cannot be detected until exogenous $BH_4$ is provided in the culture medium.

Liposome Transfection

Cells were passaged to 6 well plates at a density of $1 \times 10^5$ cells/well 24 hours prior to transfection. For 3T3 cells, each well of cells was transfected with a mixture of 1 μg plasmid DNA and 6 μg of Lipofectamine™ in OPTIMEM-I™ media for 5 hours. For rat smooth muscle cells (RSMC), a ratio of 1 μg DNA to 7 μl of Lipofectamine™ was used. Following the incubation period, the transfection solution was removed and normal growth medium replaced. The transfection efficiency was estimated by X-gal staining of pIEP-lacZ transfected cells. All studies were performed at 24–72 hours post transfection.

RNA Isolation and Northern Blot Analysis

Total cellular RNA was collected using RNAzol B from 3T3-iNOS and RSMC transfected with pCIS-GTPCH or pIEP-lacZ 72 hours post-transfection. RNA samples (20 μg) were electrophoresed on a 0.9% agarose gel and blotted to GeneScreen™. After prehybridization, the membranes were hybridized to a DNA probe as described (Geller et al., *Proc. Natl. Acad. Sci. USA*, 90, 522–26 (1993)). An 800 bp human GTPCH cDNA fragment served as the probe. The positive control for human GTPCH was RNA isolated from human hepatocytes which express GTPCH constitutively. 18S rRNA was used as a control for relative RNA loading.

Measurement of GTPCH Enzymatic Activity and Intracellular Biopterins

Forty-eight hours after transfection, NIH-3T3 cells were trypsinized and collected for GTPCH enzyme activity measurements. Trypsin was inactivated by fetal calf serum and the cells were washed with Hanks buffer. The cells were then lysed and cytosolic GTPCH activity was determined as previously described (Hatakeyama et al., *J. Biol. Chem.*, 264, 21660–64 (1989)). For total intracellular biopterin measurements, cells were treated for 60 minutes with 0.2N perchloric acid at 0° C. in the dark. The supernatants were collected and tested for total biopterins ($BH_4+BH_2$, +biopterin) as previously described (Fukushiam et al., *Anal. Biochem.*, 132, 6–13 (1983)). The cells were lysed with 0.1N NaOH and protein concentrations were measured using the BCA protein assay. Serial dilutions of bovine serum albumin served as the standards.

Assay for $NO_2^-$ and $NO_3^-$ Production

Twenty-four hours post transfection, culture medium was replaced with fresh medium, and the cells were cultured for an additional 24 hours at which time the supernatants were assayed. Measurements were also performed in the presence of L-NMA (1 mM), $BH_4$ (100 mM), and methotrexate (MTX 12.5 mM). The cells in each well were then lysed with 0.1M NaOH. Protein concentration was quantified with the BCA protein assay.

To assess the requirement for co-expression of GTPCH and iNOS in the same cell, 3T3 cells were transfected with either pIEP-lacZ or pCIS-GTPCH. After the 5 hour transfection period, the medium was changed, and the cells were overlaid with $1 \times 10^5$ cells/well of either 3T3 or 3T3-iNOS. Cells were allowed to attach overnight and $NO_2^-$ levels were measured 24 hours later.

Efficacy of GTPCH Expression Cassette Transfer

3T3 cells were used along with RSMC to test the efficacy of GTPCH expression cassette transfer. Lipofectamine transfection of 3T3, 3T3-iNOS, and RSMC resulted in a transfer efficiency of approximately 1% as determined by X-gal staining for β-galactosidase activity in pIEP-lacZ transfected cells. Northern blot analyses, using a human GTPCH cDNA probe that cross-hybridizes with rodent GTPCH, revealed no endogenous GTPCH expression in either 3T3-iNOS or RSMC groups. Endogenous GTPCH transcripts measure over 3 kb in size as seen in human hepatocytes which are abundant sources of GTPCH. However, recombinant GTPCH mRNA measures approximately 900 bp in size and was only detected in pCIS-GTPCH transfected cells. A larger 1.2 kb mRNA signal, whIch was not detectable using a rat GTPCH cDNA probe, was detected in all groups. These data show that the transferred GTPCH expression cassette is successfully transcribed.

To confirm that functional GTPCH enzyme can be generated, measurements of GTPCH enzymatic activity were performed and are summarized in Table 1. Control transfected 3T3 cells uniformly lacked GTPCH activity while pCIS-GTPCH transfected cells demonstrated levels of activity varying between 30–170 pmol/hours/mg protein which are of comparable magnitude to that measured in hepatocytes which constitutively express GTPCH.

The intracellular biopterins ($BH_4+BH_2$+biopterins) generated by GTPCH expression cassette transfer into 3T3 types cells and RSMCs are also summarized in Table 1. Dramatic increases in total intracellular biopterin concentrations were measured in pCIS-GTPCH transfected cells, regardless of the cell type. These data indicate that low efficiency GTPCH expression cassette transfer results in high level expression of functional GTPCH and completes the de novo $BH_4$ biosynthetic pathway in RSMC and 3T3 cells with the consequent generation of significant intracellular biopterins.

TABLE 1

GTPCH and Total Biopterin Transfected NIH3T3 and RSMC

| Cell Type + Transfected DNA | GTPCH Activity* (pmol/ hours/mg) | p value† | Total Biopterins* (pmol/mg) | p value‡ |
|---|---|---|---|---|
| 3T3 + pIEP-lacZ | 0 ± 0 | — | 3.0 ± 0.6 | — |
| 3T3 + pCIS-GTPCH | 169.3 ± 6.6 | 0.001 | 60.6 ± 2.6 | 0.001 |
| 3T3-iNOS + pIEP-lacZ | 0 ± 0 | — | 1.3 ± 0.6 | — |
| 3T3-iNOS + pCIS-GTPCH | 36.1 ± 6.4 | 0.01 | 25.7 ± 5.6 | 0.05 |
| RSMC + pIEP-lacZ | N.D.§ | — | 1.8 ± 1.3 | — |
| RSMC + pCIS-GTPCH | N.D.§ | — | 101.7 ± 28.3 | 0.001 |

*Values are means f standard error, n = 3, representative of 3 separate experiments
†Versus pIEP – lacZ transfected control cells
‡Versus pIEP – lacZ transfected control cells
§Not done $BH_4$ can be supplied by transfer of an GTPCH expression cassette The ability of GTPCH expression cassette transfer to reconstitute iNOS activity was assessed in 3T3iNOS cells. 3T3-iNOS cells were transfected with either pIEP-lacZ or pCIS-GTPCH and subsequent NO synthesis was measured by $NO_2^-$ accumulation in the culture supernatant. The efficiency of GTPCH expression at supporting iNOS activity in these cells was compared to the maximal NO synthesis achieved by exogenous $BH_4$ supplementation.

Transfection of 3T3-iNOS with pIEP-lacZ resulted in little $NO_2^-$ accumulation (3.9+0.4 nmol/mg protein/24 hours) and did not attenuate the response to exogenous $BH_4$ (223.6+18.9). In contrast, cells transfected with pCIS-GTPCH generated $NO_2^-$ levels comparable to that achieved with exogenous $BH_4$ (176.1±3.8 vs. 210.2±10.0, respectively). This result was surprising given the low transfection efficiency.

Low Efficiency GTPCH Expression Cassette Transfer Sustains iNOS Activity in a Population of Cells MTX inhibits dihydrofolate reductase (DHFR) which can convert dihydrobiopterin ($BH_2$), a breakdown product of $BH_4$, back to the active form of the cofactor. MTX was added to the growth medium to show the mechanism by which low efficiency GTPCH expression cassette transfer could sustain iNOS activity in a whole population of cells.

MTX reduced the amount of iNOS activity recovered by $BH_4$ supplementation by over 5-fold, indicating the majority of exogenous $BH_4$ enters cells in a form that requires metabolism by DHFR. In pCIS-GTPCH transfected 3T3iNOS cells, the MTX effect was less pronounced and only reduced iNOS activity by 50%, suggesting that $BH_4$ synthesized within cells can reach other cells as $BH_4$. Culturing 3T3-iNOS cells with conditioned medium collected from GTPCH expressing 3T3 cells, which should contain released biopterins, only reconstituted 25% of maximal iNOS activity.

No Requirement for Direct Cell-Cell Contact

The requirement for direct cell-cell contact for $BH_4$ transfer was examined by co-culturing 3T3iNOS cells with 3T3 transfected with either pIEP-lacZ or pCIS-GTPCH plasmids. Co-culturing of 3T3-iNOS cells with pIEP-lacZ transfected 3T3 cells resulted in minimal $NO_2^-$ accumulation and indicated the co-culturing process did not stimulate endogenous GTPCH activity. However, maximal iNOS activity was recovered when 3T3-iNOS cells were cocultured with pCIS-GTPCH transfected 3T3 cells, and this activity could not be further augmented by exogenous $BH_4$.

These observations show that iNOS and need not coexist in the same cell for the benefit of $BH_4$ biosynthesis to be realized. Only a few cells expressing GTPCH and synthesizing the cofactor can optimally support iNOS activity in a large population of cells.

B. Enhancement of iNOS-mediated Attenuation Of Vascular Occlusions In vivo

Ad-GTPCH is transferred to the site of iNOS delivery in vivo in order to maximize the amount of nitric oxide synthesized following iNOS expression cassette delivery by supplementing $BH_4$ in vivo.

Concomitant with iNOS expression cassette delivery to injured rat carotid arteries as described in Example 3, Ad-GTPCH at a titer of $10^7$ pfu/ml is infused into the common carotid artery through the external carotid and allowed to incubate for a 60 minute period. After the incubation period, the virus is evacuated, the external carotid artery ligated, and the flow reestablished through the common carotid artery. The collar incision is closed and the animal revived. Following a 14 day incubation, rats are sacrificed and both carotid arteries are collected for molecular and histological studies.

Collected arteries are assayed for the expression of iNOS, GTPCH, and Lac-Z in order to demonstrate that AD-GTPCH adequately promotes the exogenous expression of GTPCH at the site of infection. Furthermore, data relating to myointimal thickness for iNOS alone and for the control Ad-lacZ vector are compared with data for co-transfected arteries in order to demonstrate that exogenous GTPCH optimizes the therapeutic effect of exogenous iNOS.

Example 3

The experiments described in this example demonstrate that transfer of exogenous iNOS to the region of a wound promotes the closure or healing of the wound. The experiments demonstrate that transfer of a vector containing an iNOS expression cassette to cells associated with wounds promotes healing of both internal wounds and surface wounds.

A. Ex vivo modeling

Wounded explants were employed as a model to assess the expression of iNOS from an exogenous expression cassette transferred in situ to cells associated with wounds. Furthermore, these experiments addressed the ability of iNOS expression cassette transfer to promote healing of internal wounds.

Porcine Femoral Arteries

Femoral arteries were collected from anesthetized (sodium pentobarbital, 4 mg/kg) domestic pigs through bilateral groin incisions and immediately immersed into sterile phosphate buffered saline. The adventitia was gently dissected free, and some vessels were uniformly injured with a 4-French balloon catheter inflated to 10 atmospheres for 30 sec. All arteries were opened along the long axis, divided into 1 cm long sections, and cultured in DMEM, 20% FCS, 100 units/ml penicillin, 100 μg/ml streptomycin, and 4 mM L-glutamate at 37° C. as previously described (Takeshita et al., *J. Clin. Invest.*, 93, 652–61 (1994)).

On culture day, some arterial segments were incubated with 2 ml of either DFG-iNOS-Neo or MFG-lacZ viral supernatant (both titers $10^6$ PFU/ml) supplemented with polybrene (8 μg/ml) for 6 hours. Following infection, the vessels were transferred to fresh culture dishes to remove any explanted cells and were maintained in organ culture for a total of 14 days with daily media changes. After initial observations that $NO_2^- + NO_3^-$ release from the DFG-iNOS-Neo transfected vessels was $BH_4$-dependent, $BH_4$ (100 µM) was supplemented on a daily basis to all the cultures. L-NMA (0.5 mM) was added to some vessel preparations. On day 14, culture supernatants were collected for $NO_2^- + NO_{3-}$ and cGMP determinations. cGMP levels were measured with a commercial radioimmunoassay.

To evaluate efficiency of MFG-lacZ infection, vessel segments were fixed in 0.5% glutaraldehyde for 30 minutes and stained for β-galactosidase activity with X-gal. DFG-iNOS-Neo segments were fixed in 2% paraformaldehyde for 1 hour at 4° C. and cryoprotected in 30% sucrose overnight at 4° C. Vessels were then quick frozen with HistoFreeze™2000 and 5 µM cryosections cut. Sections were mounted on glass slides, permeabilized with 2% paraformaldehyde/0.1% Triton-X100, blocked with 5% goat serum, and then incubated with the primary monoclonal antimurine iNOS antibody previously used for Western blot analysis. The antibody staining was visualized with immunoperoxidase. To measure myointimal thickness, semi-serial sections were incubated for 60 minutes with rhodamine phalloidan, which binds to actin. These preparations were visualized with indirect fluorescence microscopy and recorded by a Sony DXC 930 camera linked to a computer. The neointimal thickness was quantified with the Optimas™ program (Optimal Corp.; Seattle, Wash.) at 25 random sites along the length of each vessel segment and calculated as the mean of all the measurements.

Some vessels were homogenized with a polytron, and the RNA was extracted with RNAzol as described in Example 2. PCR amplification of human iNOS, as described in Example 1.J was performed. PCR amplification for Neo mRNA, unique to the DFG-iNOS-Neo virus, was performed as another marker for expression of the iNOS transgene (Neo PCR product=728 bp). PCR products were visualized on a 1.5% agarose gel.

Human Coronary Arteries

Human coronary arteries were extracted from the extirpated hearts of patients undergoing cardiac transplantation. Immediately upon extirpation, the left anterior descending coronary artery was sharply dissected from the left ventricle. The anterior and posterior tibial arteries were obtained from patients undergoing lower extremity amputations immediately following the amputation. All vessels were immediately placed in normal saline solution. A 2 or 4 French catheter was placed into the vessel segment and inflated with saline from a 1 cc syringe with the balloon remaining inflated for 30 seconds. Under sterile conditions, the adventitia was sharply dissected from the vascular segments. The vessels were then divided into 1 cm sections for placement into the organ culture system. The organ culture system contained DMEM supplemented with 20% fetal calf serum, 2 mM L-glutamine, 100 units/ml penicillin and 100 µg/ml streptomycin.

Once placed into the organ culture the media was changed daily. On day 5, the vessels were infected with DFG-iNOS-Neo. One ml of the retroviral supernatant containing $10^6$ CFU/ml was added to each vessel being transfected. On the following day, the viral supernatant was removed and the routine media solution added to the organ bath. Daily media changes were again performed with 100 µM $BH_4$ being added to each well. On day 14, the media were collected for total nitrite and nitrate as well as cGMP measurements. The vessels are then frozen for histologic analysis.

To examine the thickness of the medial layer following the arterial wounding and ensuing 14 days in culture, the vessels were sectioned into 5 µm sections. The vessels were washed twice with 1% PBS solution and stained with rhodamine phalloidan for 60 minutes. The sections are washed again with 1% PBS and cover slipped. The segments were prepared and examined as described above.

Expression of iNOS in Cultured Vessels

Following balloon catheter-induced vascular injury and viral infection five days after injury, arterial segments infected with DFG-iNOS-Neo released 3–4 fold more $NO_2^- + NO_3^-$ vs. uninjured vessels or MFG-lacZ-infected segments (Table 2) as measured on culture day 14. More dramatically, cGMP release by DFG-iNOS-Neo infected arteries increased by 15 fold over that measured in either uninjured or injured control vessel segments. Inclusion of L-NMA in the culture media inhibited both $NO_2^- + NO_3^-$ and cGMP release.

Staining for β-galactosidase or iNOS in the infected arterial segments showed an estimated infection efficiency of 0.5–1%. The majority of cells expressing either enzyme were found to be located in the superficial neointimal region. Transgene expression was further confirmed by RT-PCR amplification for human iNOS message. The predicted 316 bp iNOS PCR product was strongly detected only in DFG-iNOS-Neo infected vessel segments. A very low level of iNOS mRNA was detected in MFG-lacZ infected vessels. Detectable iNOS expression by PCR amplification in control vessels may reflect a low level induction secondary to balloon-catheter injury. However, amplification for Neo sequences unique to the DFG-iNOS-Neo retrovirus revealed expression of the expected 728 bp fragment solely in the DFG-iNOS-Neo infected vessels, thus providing added confirmation of expression of the transferred genes.

Figure 6A:
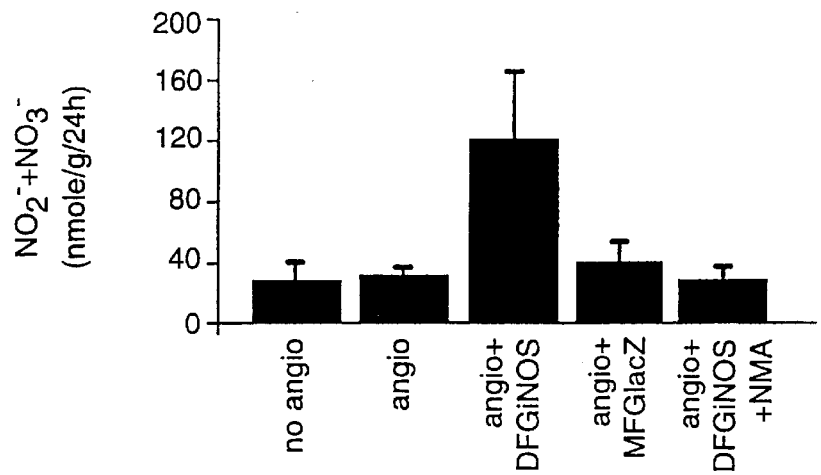
FIGS. 6A–C are charts showing $NO_2^- + NO_3^-$ production (FIG. 6A), cGMP production (FIG. 6B), and myointimal thickness (FIG. 6C) in cultured porcine femoral arteries uninfected or infected with DFG-iNOS-neo or MFG-lacZ either exposed to arterial injury.
Figure 6B:
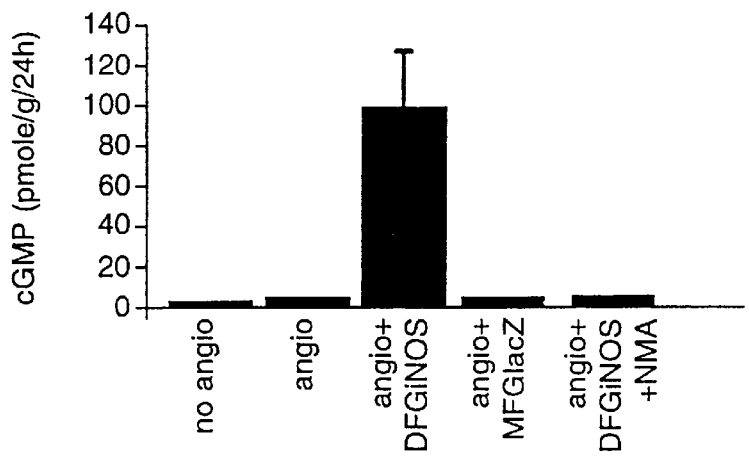
Figure 6C:
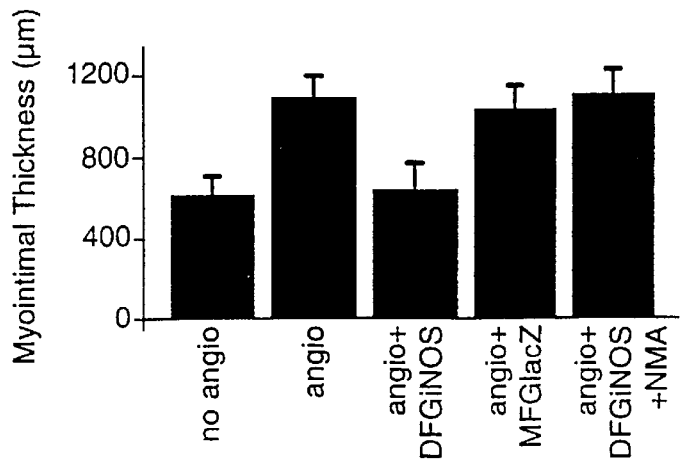
Figure 7A:
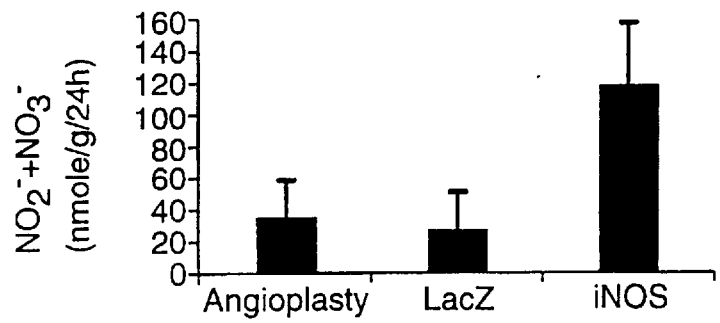
FIGS. 7A–C are charts showing $NO_2^- + NO_3^-$ production (FIG. 7A), cGMP production (FIG. 7B), and myointimal thickness (FIG. 7C) in cultured human tibial and coronary arteries uninfected or infected with DFG-iNOS-neo or MFG-lacZ either exposed to arterial injury.
Figure 7B:
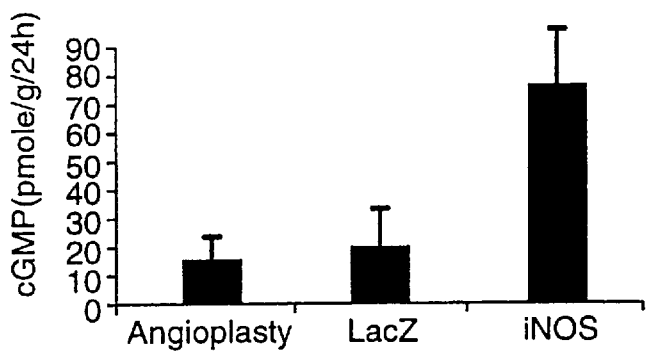
Figure 7C:
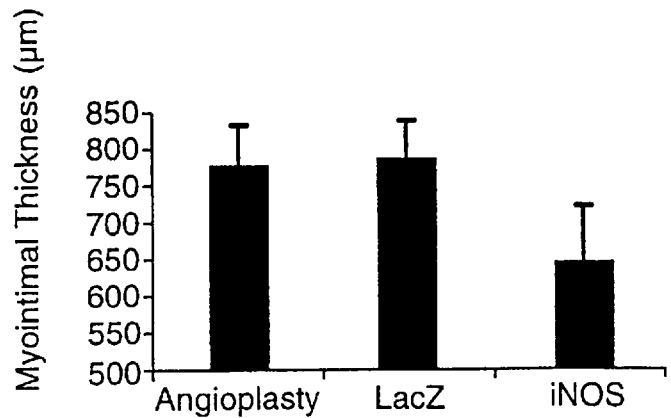

FIGS. 6A–C and FIGS. 7A–C show data generated from in vitro cultured porcine arteries infected with DFG-iNOS-Neo (FIGS. 6A–C) as well as diseased human coronary and tibial arteries infected with DFG-iNOS-Neo (FIGS. 7A–C). The control construct in FIGS. 6A–C and FIGS. 7A–C was MFG-lacZ. FIGS. 6A and 7A show that total nitrite production was significantly elevated in the vessels infected with DFG-iNOS-Neo as compared to vessels undergoing angioplasty alone or infected with MFG-lacZ. The elevation in total NO production was abrogated by adding the NO inhibitor LNMA. Similarly cyclic GMP levels were significantly elevated in infected arterial segments when compared to uninfected segments and segments infected with the control retrovirus MFG-lacZ.

TABLE 2

Total Nitrogen Oxide and cGMP Production By Porcine Arterial segments

| Treatment Groups | Total $NO_2$ and $NO_3$ (pmol/mg/24 hours) | p value † | cGMP (fmol/mg/24 hours) | p value † |
|---|---|---|---|---|
| Control | 29.7 ± 6.5* | — | 5.2 ± 2.8 | — |
| Injury alone | 35.4 ± 8.4 | NS | 7.3 ± 3.4 | NS |
| Injury + MFG-lacZ | 40.1 ± 5.2 | NS | 6.8 ± 2.9 | NS |
| Injury + DFGiNOS + | 121.9 ± 43.1 | 0.001 | 101.3 ± 12.1 | 0.002 |
| Injury + DFGiNOS + L-NMA* | 37.4 ± 8.2 | NS | 5.6 ± 4.2 | NS |

*Values are means ± standard deviations, n = 4, representative of 3 separate experiments
† Versus uninjured control arterial segments Effect on Intimal Hyperplasia As indicated in FIG. 6C, injury of rat arteries resulted in a significant increase in the total thickness of the medial layer. Infection with the DFG-iNOS-Neo vector resulted in the inhibition of this proliferative process. The medial thickness in vessels infected with DFG-iNOS-Neo and grown in L-NMA or vessels infected with MFG-lacZ were similar to the angioplasty control segments.

Balloon catheter injury of human coronary or tibial arterial resulted in a significant increase in myointimal thickness, as determined by rhodamine phalloidan staining in both wounding alone or wounding followed by infection with MFG-lacZ (FIG. 7C). In contrast, the proliferative response to balloon wounding in arteries subsequently infected with DFG-iNOS-Neo was markedly attenuated and essentially indistinguishable from uninjured vessels. The inhibitory effect of DFG-iNOS-Neo infection on myointimal thickening was completely abrogated by L-NMA administration, indicating the effect was dependent on NO synthesis.

Discussion

These data demonstrate that an iNOS expression cassette can produce iNOS in human or porcine cells associated with explanted arterial segments. Furthermore, these data demonstrate that transfer of an iNOS expression cassette effectively transfers iNOS activity to cells in the region of the explant. Lastly, these data demonstrate that products exogenously supplied iNOS facilitate the proper reconstruction of tissue in the region of vascular injury and facilitates the healing of wounds associated with vascular injury.

B. Internal Wound Healing

The ability of exogenous iNOS to facilitate the healing of internal wounds was investigated by transferring iNOS expression cassettes to wounds associated with the site of vascular injury in animal models. These experiments monitored the effectiveness of iNOS at promoting proper regrowth of injured vascular tissue.

Promotion of Internal Wound Healing

Rats were anesthetized with Nembutal and the left common carotid artery was exposed through a collar incision. A 2 French Fogarty catheter was introduced through the left external carotid artery into the common carotid and the balloon was inflated to create a vascular injury. Similarly, domestic pigs were anesthetized with sodium pentobarbital and bilateral iliac arteries were exposed through a low midline abdominal incision. A small arteriotomy was created through which a 4 French Fogarty catheter was introduced. Inflation of the Fogarty was used to create a vascular injury.

In Vivo Transfer of iNOS

In vivo transfer of an iNOS expression cassette was performed with Ad-iNOS. Control animals included animals subjected to carotid artery injury alone or subjected to injury followed with infection with Ad-lacZ control virus.

Following balloon injury of rat arteries, Ad-iNOS or Ad-lacZ at a titer of $10^7$ pfu/ml was infused into the common carotid artery through the external carotid and allowed to incubate for a 60 minute period. After the incubation period, the virus was evacuated, the external carotid artery ligated, and the flow reestablished through the common carotid artery. The collar incision was closed and the animal revived. Rats were housed for a total of 14 days, at which time they were sacrificed, and both carotid arteries were collected for molecular and histological studies.

Ad-iNOS or Ad-lacZ ($10^7$ pfu/ml) was instilled into an isolated segment of the pig iliac artery and permitted to incubate for 60 minutes. After the incubation period, the virus was evacuated, the arteriotomy repaired, and flow reestablished. One iliac vessel served as the experimental side while the contralateral served as the control. Pigs were housed for periods of time varying between 1, 3 and 6 weeks. At the end of these time periods, the pigs were sacrificed, and bilateral iliac arteries were collected for molecular and histological studies.

For histologic evaluation, the vessels were fixed in paraformaldehyde and sucrose and then cryopreserved. Following sectioning, tissues are stained with hematoxylin and eosin. Intimal and medial thickness is quantified using computer imaging programs. LacZ staining is performed using X-gal to detect β-galactosidase activity. Immunostaining for iNOS was performed with a polyclonal iNOS antibody against murine iNOS that detects human iNOS followed by treatment with a secondary antibody complexed to horseradish peroxidase. Cellular proliferation is quantified with bromodeoxyuridine (BrdU) or by immunostaining with an antibody directed against proliferating cell nuclear antigen (PCNA).

Expression of iNOS in Infected Vessels

RT-PCR conducted 14 days post-infection from RNA isolated from vascular tissue at the site of injury demonstrated the expression of human iNOS from vessels infected with the Ad-iNOS vector, but not from control vessels. Furthermore, expression of iNOS was confined to the region of the vessels into which Ad-iNOS had been transferred.

iNOS-Mediated Healing of Wounded Vessels

Histologic examination of the experimental carotid arteries 14 days following injury and expression cassette transfer revealed that arterial injury resulted in marked intimal hyperplasia with a neointima measuring approximately twice the width of the medial layer. Animals treated with the control Ad-lacZ virus still responded to arterial injury with the formation of a thick neointima that resembled animals subjected to injury alone. However, the carotid arteries that were treated with Ad-iNOS demonstrated a complete inhibition of this proliferative process with no evidence of neointimal formation. These carotid arteries resembled uninjured arteries.

Similar results were obtained by direct in situ infection of porcine arterial vascular cells with Ad-iNOS and Ad-lacZ. Subsequent to mechanical injury of a porcine arterial segment either Ad-iNOS or Ad-lacZ were transferred to intimal vascular cells at the site of catheterization. These results indicate a marked reduction in myointimal hyperplasia within in situ infected Ad-iNOS arterial segments in comparison to in situ infected Ad-lacZ arterial segments.

Discussion

These data demonstrate that an iNOS expression cassette can produce iNOS in vivo in the region of a wound, notably a wound associated with vascular injury. Furthermore, these results show successful reduction in myointimal hypertrophy or cicratization following balloon-catheter induced arterial injury with human iNOS expression cassette transfer, despite low transfer efficiency. These data demonstrate that exogenously supplied iNOS facilitates the proper reformation of injured vascular tissue, and this promotes the healing of internal wounds.

C. Promotion Of External Wound Healing

Methods iNOS KO mice or control mice were subjected to a 2 cm×2 cm full thickness wound to the back. Subsequently, a sterile saline solution containing either the Ad-iNOS vector or the control vector (Ad-lacZ) at $2\times10^7$ pfu was applied topically to the region of the wounds. Animals were then bandaged identically, the rate of wound closure monitored, and the tissue assayed for iNOS expression.

Time-dependent expression of iNOS was monitored in order to correlate the acceleration of wound healing with iNOS expression. Wound tissue was collected from all experimental groups at 2-day intervals. Total cellular RNA was harvested from these cells and subjected to RT-PCR as described above in Example 1, using primers specific for human iNOS, murine iNOS, and β-actin.

Expression of iNOS in Wounds

In agreement with published results (Carter et al., Biochem. J., 304, 201–04 (1994)), wounding was associated with a marked increase in native iNOS expression in WT animals; maximal levels of native iNOS expression were observed at 4–6 days post-wounding, and iNOS expression was detected for up to 10 days post wounding. KO mice expressed no detectable iNOS signal. Human iNOS signal was detected from cells of both KO and WT mice into which the iNOS expression cassette had been transferred. Peak expression of human iNOS was observed 2–4 days post wounding and was detectable for up to 14 days. No human iNOS expression was detected from cells of untreated WT mice or from cells into which the control cassette was transferred.

Time to Wound Closure

Data relating to time to wound closure are set forth in Table 3. While control mice required 17.00 days for complete wound closure, KO mice required 22.33 days. Transfer of a-lacZ expression cassette to cells associated with the wounds resulted in no significant effect on wound closure. In contrast, KO mice required 15.60 days for complete wound closure after transfer of an iNOS expression cassette to the cells associated with the wounds, while similarly treated control mice required 15.77 days for complete wound closure.

TABLE 3

Days to wound closure in mice and the effect of iNOS expression cassette transfer.

| Group | Days to Wound Closure | | | |
|---|---|---|---|---|
| | 30% | 50% | 80% | 100% |
| WT | 3.53 ± 0.10 | 6.10 ± 0.23 | 9.91 ± 0.34 | 17.00 ± 0.37 |
| KO | 4.40 ± 0.30 | 7.03 ± 0.40 | 11.97 ± 0.55† | 22.33 ± 0.80* |
| WT + Ad-lacZ | 4.33 ± 0.25 | 5.78 ± 0.25 | 9.33 ± 0.11 | 17.33 ± 0.57 |
| WT + Ad-iNOS | 4.04 ± 0.22 | 6.21 ± 0.27 | 9.22 ± 0.38 | 15.77 ± 0.22 |
| KO + Ad-lacZ | 4.93 + 0.36 | 7.34 ± 0.38 | 11.74 ± 0.36† | 20.22 ± 0.61† |
| KO + Adi-NOS | 4.38 ± 0.36 | 6.23 ± 0.37 | 9.31 ± 0.36 | 15.60 ± 0.49 |

Values = mean ± SEM, n = 9 per group
*$p < 0.001$ vs WT groups and KO + Ad-iNOS
†$p < 0.01$ vs WT groups and KO + Ad-iNOS Discussion These data demonstrate that transfer of exogenous iNOS to an external wound accelerates healing. The result is most striking in patients experiencing reduction in endogenous iNOS production. These data further demonstrate that an effective mode of supplying exogenous iNOS is by transferring an iNOS expression cassette to cells associated with the wound. These dana further demonstrate that wound healing is positively correlated with induction of iNOS expression within the cells associated with the wound.

Example 4

The experiments described in this Example demonstrate that transferring a vector comprising an iNOS expression cassette to cells associated with a graft eliminates vasculopathy (which would otherwise occur) following surgical implantation.

From donor rats, a 3 cm segment of descending thoracic aorta was excised, and perfused with a sterile saline solution. These graft aortas were implanted into the intrafrenal aortas of the recipients in an end-to-end fashion using continuous 9-0 nylon suture.

Male rats 1–3 months of age, 200–300 grams were employed as donors and as recipients of grafts. For heterotropic transplantation, Wistar Furth (WF) rats were employed as graft donors, and ACI rats were employed as recipients. ACI to WR grafts were used for allografts and ACI-ACI transplantation for syngenic controls.

Prior to implantation, the grafts were incubated for one hour in a saline solution containing $2 \times 10^7$ pfu adenoviral vector. For experimental groups, the vector was Ad-iNOS, containing the iNOS expression cassette. For controls, the vector was Ad-lacZ.

Four weeks post-implantation, grafts were removed and examined histologically for the development of allograft vasculopathy. This was accomplished by staining the vessels with a Verhoff/van Geison stain and then measuring the intimal and medial layer thickness. From these measurements, the intima/media (I/M) ratio was calculated.

Figure 8:
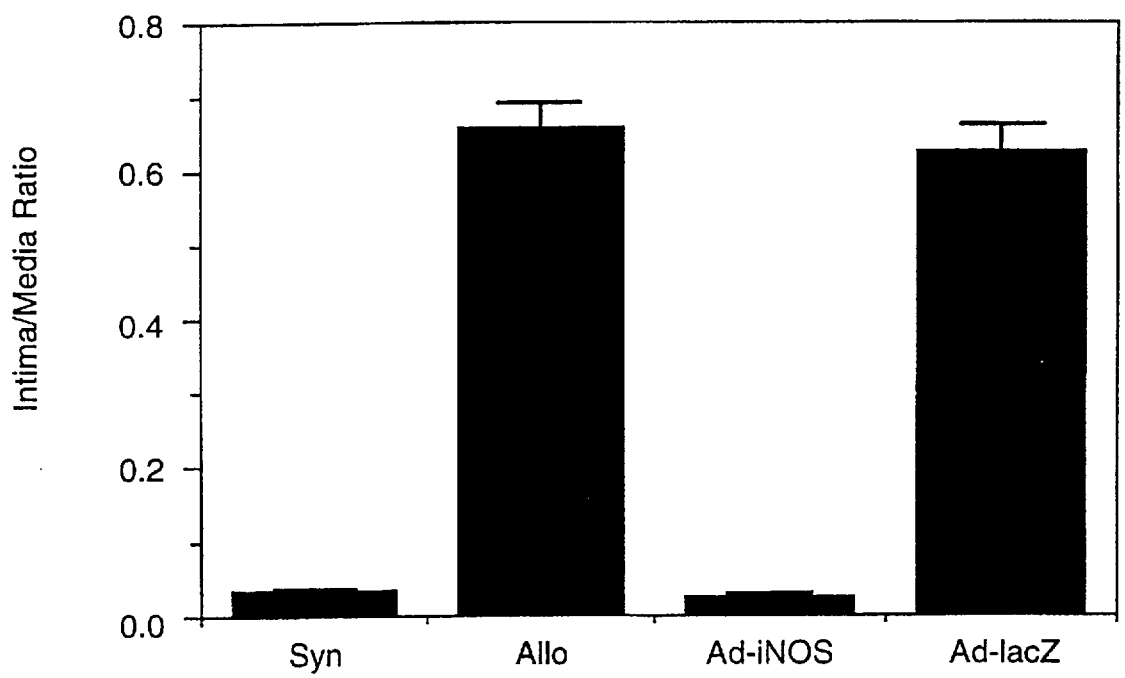
FIG. 8 is a chart showing the effect of expression cassette transfer on allograft vasculopathy in rat aortic grafts uninfected or infected with Ad-iNOS or Ad-lacZ.

Data relating to the effect of iNOS transfer on Allograft vasculopathy are presented graphically in FIG. 8.

The syngenic controls displayed a neoinima of $0.036 \pm 0.005$ μm while the allogenic control and the graft treated with Ad-LacZ displayed intimal thickness of $0.66 \pm 0.029$ μm, and $0.63 \pm 0.031$ μm, respectively. Allogenic grafts treated with Ad-iNOS displayed average intimal thickness of $0.029 \pm 0.002$ μm. Thus, both the untreated allograft group and those treated with Ad-lacZ exhibited marked neointimal hyperplasia 4 weeks post-implantation (I/M ratio>0.6). In contrast, syngraft controls exhibited negligible intimal hyperplasia in the same period (I/M ratio>0.05). Strikingly, the allograft group treated with Ad-iNOS exhibited no appreciable neointimal hyperplasia (I/M ratio>0.05), and was on par with results seen with syngenic grafts.

These data indicate that transferring a vector comprising an iNOS expression cassette to cells associated with a graft substantially attenuates or eliminates vasculopathy in the region of the graft.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

What is claimed is:

1. A method of promoting the closure of a wound in a patient which comprises transferring exogenous iNOS to the region of said wound.

2. The method of claim 1 wherein said wound is an external wound.

3. The method of claim 2 wherein exogenous iNOS is transferred to the region of said wound by topical administration of iNOS to the region of the wound.

4. The method of claim 1 wherein said wound is an internal wound.

5. The method of claim 1 wherein said patient is human.

6. The method of claim 1 wherein said patient is deficient for NO production.

7. The method of claim 1 which further comprises transferring exogenous $BH_4$ to the region of said wound such that iNOS enymatic activity is enhanced.

8. The method of claim 12 wherein said wound is an external wound and wherein exogenous $BH_4$ is transferred to the region of said wound by topical administration of $BH_4$ to the region of the wound.

* * * * *